(12) United States Patent
Ueno et al.

(10) Patent No.: US 7,154,989 B2
(45) Date of Patent: Dec. 26, 2006

(54) RADIOLOGICAL IMAGING APPARATUS

(75) Inventors: Yuuichirou Ueno, Hitachi (JP); Hiroshi Kitaguchi, Naka (JP); Kensuke Amemiya, Hitachinaka (JP); Kikuo Umegaki, Hitachinaka (JP); Norihito Yanagita, Hitachi (JP); Shinichi Kojima, Hitachi (JP); Kazuma Yokoi, Higashikanesawa (JP)

(73) Assignee: Hitachi, Ltd., Tokyo (JP)

( * ) Notice: Subject to any disclaimer, the term of this patent is extended or adjusted under 35 U.S.C. 154(b) by 50 days.

(21) Appl. No.: 10/688,977

(22) Filed: Oct. 21, 2003

(65) Prior Publication Data

US 2004/0125915 A1 Jul. 1, 2004

(30) Foreign Application Priority Data

Oct. 23, 2002 (JP) ............................ 2002-307785

(51) Int. Cl.
*A61B 6/00* (2006.01)
(52) U.S. Cl. .................... 378/19; 250/363.04
(58) Field of Classification Search ................. 378/19; 250/363.03, 363.04, 370.09, 370.1, 367
See application file for complete search history.

(56) References Cited

U.S. PATENT DOCUMENTS

| | | | | |
|---|---|---|---|---|
| 4,639,599 A * | 1/1987 | Ichihara | ................. | 250/363.04 |
| 4,677,299 A * | 6/1987 | Wong | ..................... | 250/363.03 |
| 4,843,245 A | 6/1989 | Lecomte | | |
| 5,907,156 A | 5/1999 | Nishizawa et al. | | |
| 6,175,611 B1 * | 1/2001 | Melen et al. | ................. | 378/19 |
| 6,448,559 B1 | 9/2002 | Saoudi et al. | | |
| 6,661,866 B1 * | 12/2003 | Limkeman et al. | ........... | 378/19 |
| 2002/0090050 A1 | 7/2002 | Nutt et al. | | |
| 2002/0191734 A1 | 12/2002 | Kojima et al. | | |
| 2003/0108147 A1 | 6/2003 | Kojima et al. | | |
| 2003/0179853 A1 | 9/2003 | Amemiya et al. | | |

FOREIGN PATENT DOCUMENTS

| | | |
|---|---|---|
| EP | 0-219-648 | 4/1987 |
| GB | 2-058-511 | 4/1981 |
| JP | 6151585 | 3/1986 |
| JP | 62052479 | 3/1987 |
| JP | 7-20245 | 1/1995 |
| JP | 9-5441 | 1/1997 |

OTHER PUBLICATIONS

IEEE Transaction on Nuclear Science, NS-21, No.1, pp. 228-229.

* cited by examiner

*Primary Examiner*—Edward J. Glick
*Assistant Examiner*—Jurie Yun
(74) *Attorney, Agent, or Firm*—Dickstein Shapiro LLP

(57) ABSTRACT

The image pickup apparatus of the radiological imaging apparatus of the present invention includes many detector units, a ring-shaped detector support member and an X-ray source circumferential transport apparatus. Each of the detector units is attached to the detector support section in a detachable manner. A plurality of radiation detectors provided for the detector units are arranged in three layers in the radius direction of the detector support member and in three columns in the axial direction of the detector support member. Since the radiation detectors are arranged in three layers in the radius direction, it is possible to recognize the detection position of radiation in the radius direction in detail. Furthermore, since the detector units are attached in a detachable manner, it is easy to replace damaged radiation detectors.

28 Claims, 10 Drawing Sheets

RADIOLOGICAL IMAGING APPARATUS

BACKGROUND OF THE INVENTION

The present invention relates to a radiological imaging apparatus, and more particularly, to a radiological imaging apparatus ideally applicable to radiological two-dimensional image pickup apparatus, X-ray computed tomography (hereinafter referred to as "X-ray CT"), positron emission computed tomography (hereinafter referred to as "PET") and single photon emission computed tomography (hereinafter referred to as "SPECT").

Among typical radiological imaging apparatuses, which is a non-invasive imaging technology for examining functions and conformation of the body of a medical examinee, are radiological two-dimensional image pickup apparatus, X-ray CT, PET and SPECT, etc.

PET inspection is an inspection consisting of administering radiopharmaceutical (hereinafter referred to as "PET radiopharmaceutical") including positron emitters ($^{15}$O, $^{13}$N, $^{11}$C, $^{18}$F, etc.) to the examinee and examining locations in the body where more PET radiopharmaceutical is consumed. The PET inspection is an action of detecting γ-rays emitted from the body of the examinee caused by PET radiopharmaceutical using a radiation detector. More specifically, one positron emitted from a positron emitter in the PET radiopharmaceutical couples with an electron of a neighboring cell (cancerous cell), disappears and at the same time irradiates a pair of γ-rays (called "γ-ray pair") having energy of 511 keV. These γ-rays are emitted in directions opposite to each other (180°±0.6°). Detecting this pair of γ-rays using a radiation detector makes it possible to know between which pair of radiation detectors the positron is emitted. Detecting those many γ-ray pairs makes it possible to identify locations where more PET radiopharmaceutical is consumed. For example, when PET radiopharmaceutical created by coupling positron emitters and carbohydrate is used, it is possible to discover cancer focuses having hyperactive carbohydrate metabolism. One example of the radiological imaging apparatus used for PET is described in JP-A-7-20245. The data obtained is converted to data of each voxel using the Filtered Back Projection method described in non-patent document 1 (IEEE Transaction on Nuclear Science, Vol. NS-21, pp. 228–229). Positron emitters ($^{15}$O, $^{13}$N, $^{11}$C and $^{18}$F, etc.) used for the PET inspection have a half life of 2 to 110 minutes.

The SPECT administers radiopharmaceutical (hereinafter referred to as "SPECT radiopharmaceutical") including single photon emitters ($^{99}$Tc, $^{67}$Ga, $^{201}$Tl, etc.) and matters (e.g., carbohydrate) having a property of concentrating on a specific tumor or specific molecule to an examinee and detects γ-rays emitted from the emitters using a radiation detector. The energy of γ-rays emitted from the single photon emitters often used for inspection using the SPECT is around several 100 keV. In the case of the SPECT, single γ-rays are emitted, and therefore it is not possible to obtain their angle of incidence upon the radiation detector. Thus, angle information is obtained by detecting only γ-rays incident from a specific angle through a collimator using the radiation detector. The SPECT is an inspection method of identifying locations where more SPECT radiopharmaceutical is consumed by detecting γ-rays generated in the body caused by the SPECT radiopharmaceutical. One example of the radiological imaging apparatus used for the SPECT is described in JP-A-9-5441. The SPECT also converts data obtained to data of each voxel using a method such as Filtered Back Projection. The SPECT may also take transmission images. $^{99}$Tc, $^{67}$Ga and $^{201}$Tl used for the SPECT have a half life longer than that of radionuclide used for the PET, for example, 6 hours to 3 days.

SUMMARY OF THE INVENTION

There is a demand for further improvement of diagnostic accuracy in the position and size, etc., of an affected area such as malignant tumor and there is also a demand for improvement of accuracy of images including the affected area created by a radiological imaging apparatus. It is also an important challenge to allow a damaged radiation detector to be replaced in a short time.

It is an object of the present invention to provide a radiological imaging apparatus capable of improving the accuracy of an image created and easily replacing a damaged radiation detector.

A feature of the present invention to attain the above-described object is that a detection unit is attached to a detector support member in a detachable manner and the detection unit is provided with a plurality of radiation detectors that detect radiation and other radiation detectors that detect radiation which has passed through some of the above described radiation detectors.

Since the other radiation detectors for detecting radiation that has passed through some radiation detectors are provided, it is possible to detect radiation emitted from the examinee by the some radiation detectors or the other radiation detectors and accurately confirm the position the radiation has reached from the some radiation detectors facing the examinee in the depth direction (position at which the radiation has been detected). Thus, it is possible to obtain an accurate image illustrating the condition of the body of the examinee. Furthermore, since the detector unit is attached to the detector support member in a detachable manner, a damaged radiation detector can be replaced easily.

Other objects, features and advantages of the invention will become apparent from the following description of the embodiments of the invention taken in conjunction with the accompanying drawings.

DESCRIPTION OF THE INVENTION (Embodiment 1)

Figure 1:
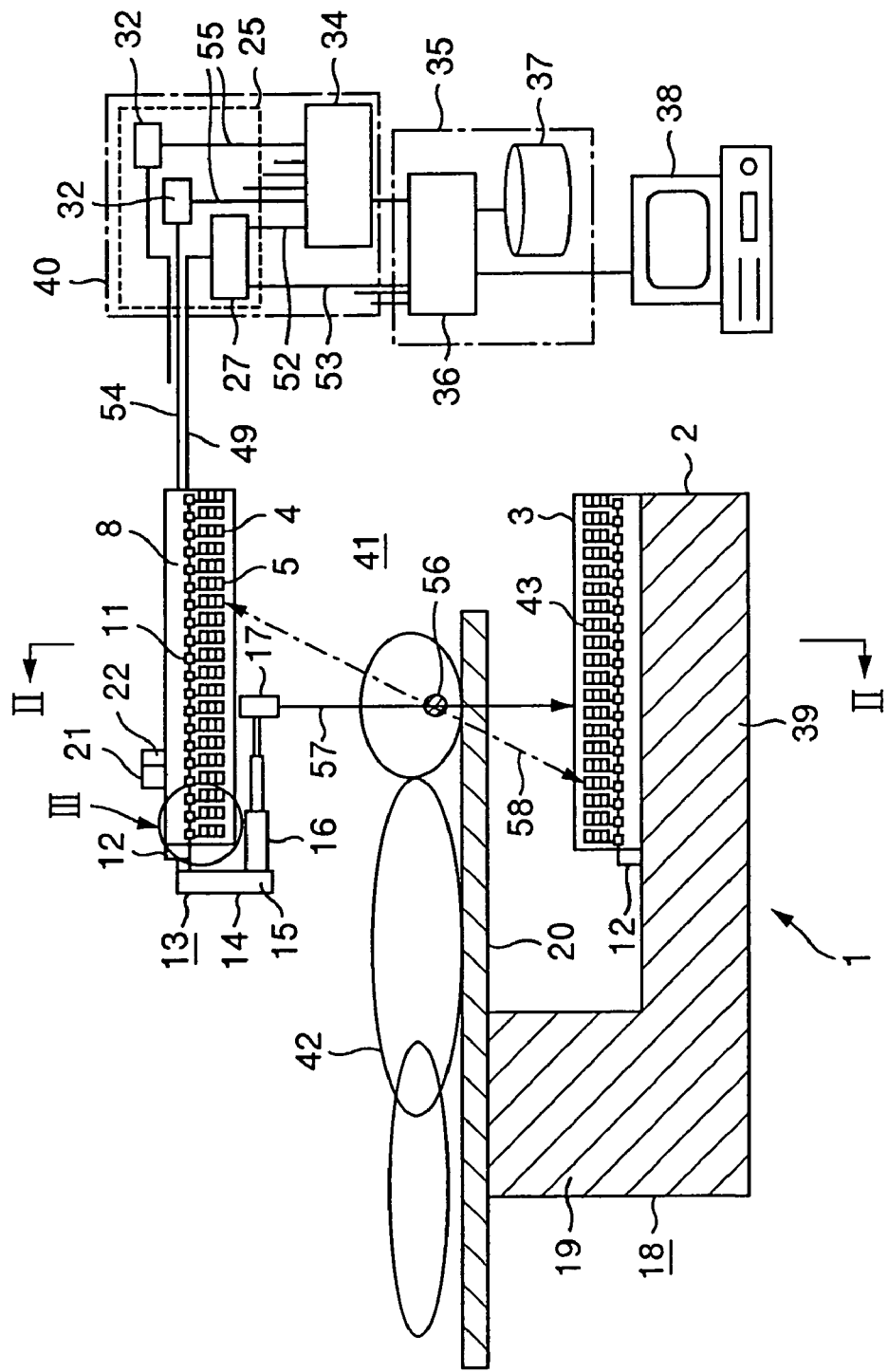
FIG. 1 is a longitudinal sectional view of a radiological imaging apparatus of Embodiment 1 which is a preferred embodiment of the present invention.
Figure 2:
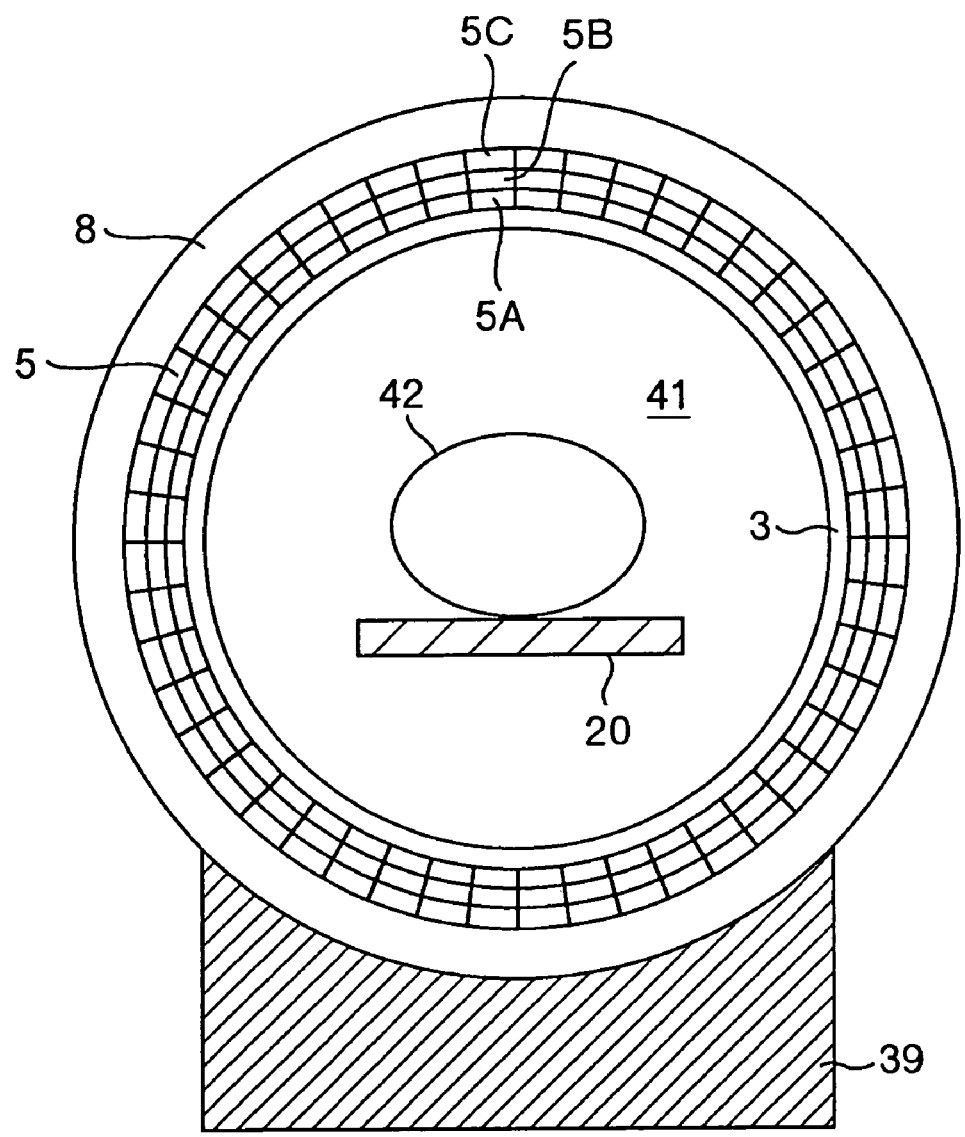
FIG. 2 is a sectional view along a line II—II of FIG. 1.

With reference now to FIG. 1 and FIG. 2, a radiological imaging apparatus which is a preferred embodiment of the present invention will be explained below. A radiological imaging apparatus 1 of this embodiment is used for a PET inspection. The radiological imaging apparatus 1 is provided with an image pickup apparatus 2, a signal processing apparatus 40, a tomographic image creation apparatus 35, an examinee holding apparatus 18, a drive apparatus control apparatus 21 and an X-ray source control apparatus 22. The examinee holding apparatus 18 includes a bed 20 on top of a bed support section 19 in such a way that the bed 20 is movable in the longitudinal direction.

Figure 3:
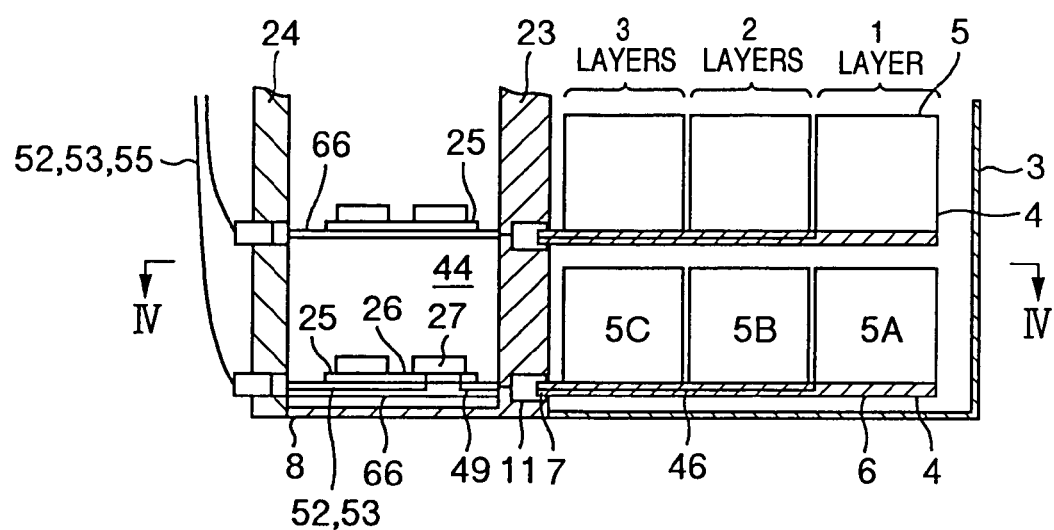
FIG. 3 is an enlarged view of the section III of FIG. 1.
Figure 4:
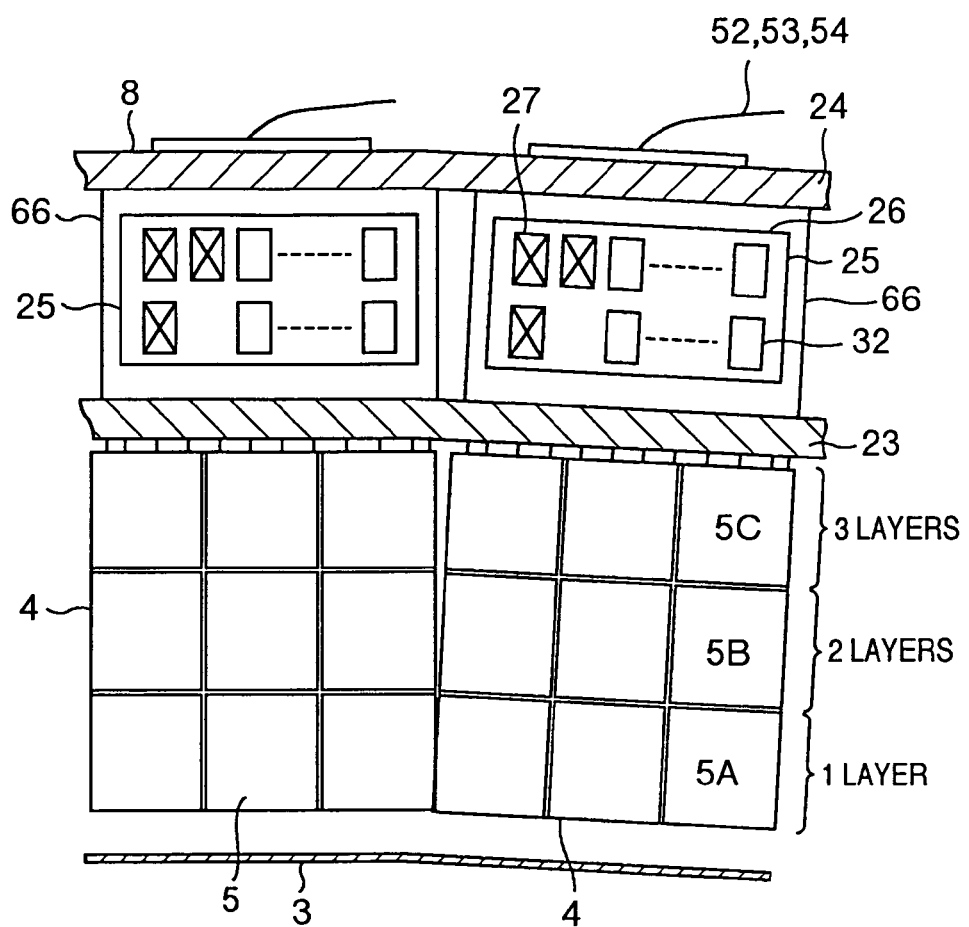
FIG. 4 is a sectional view along a line IV—IV of FIG. 3.

The image pickup apparatus 2 includes a casing 3, many detector units 4, a ring-shaped detector support member 8 and an X-ray source circumferential transport apparatus 13. As shown in FIG. 3 and FIG. 4, the detector support member 8 includes a ring-shaped detector support section 23 attached to a support member 39 and a cover member 24. The cover member 24 is attached to the detector support section 23, covering a signal discrimination unit housing space 44 formed in the detector support section 23.

The X-ray source circumferential transport apparatus 13 is provided with a guide rail 12 and an X-ray source apparatus 14. The ring-shaped guide rail 12 is attached to the examinee holding apparatus 18 on the side of the detector support member 8, more specifically, on the side of the detector support section 23 so as to surround a through hole section 41 into which the bed 20 is inserted. The X-ray source apparatus 14 includes an X-ray source drive apparatus 15, a telescopic arm 16 and an X-ray source 17. The X-ray source drive apparatus 15 is attached to the guide rail 12 in a movable manner. The X-ray source drive apparatus 15 includes a pinion (not shown) which engages with the rack of the guide rail 12 and a motor which rotates this pinion through a deceleration mechanism. The telescopic arm 16 is attached to a casing (not shown) of the X-ray source drive apparatus 15 and can zoom in and out in the horizontal direction. The X-ray source 17 is attached to the end of the telescopic arm 16.

Though not shown, the X-ray source 17 includes a publicly known X-ray tube. This X-ray tube is provided with an anode, a cathode, a current source for the cathode and a voltage source for applying a voltage to between the anode and cathode inside the external cylinder. The cathode is a tungsten filament. When a current flows from the current source to the cathode, electrons are emitted from the filament. These electrons are accelerated by a voltage (several hundred kV) applied from the voltage source to between the cathode and anode and collide with the anode (W, Mo, etc.), the target. Collision of electrons with the anode produces X-rays of 80 keV. These X-rays are radiated from the X-ray source 17.

The tomographic image creation apparatus 35 is provided with a computer 36 and a storage apparatus 37. The computer 36 is connected to a coincidence counter 34 and the storage apparatus 37 is connected to the computer 36. The computer 36 is a tomographic image creation section. A display device 38 is connected to the computer 36.

Figure 5:
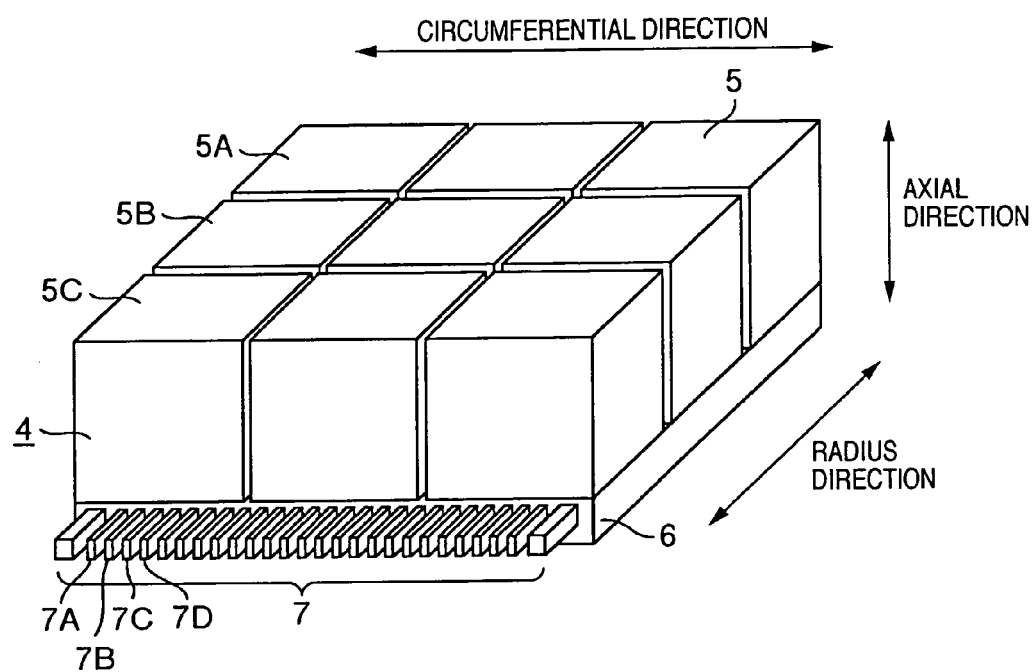
FIG. 5 is a perspective view of the detector unit in FIG. 1.
Figure 6:
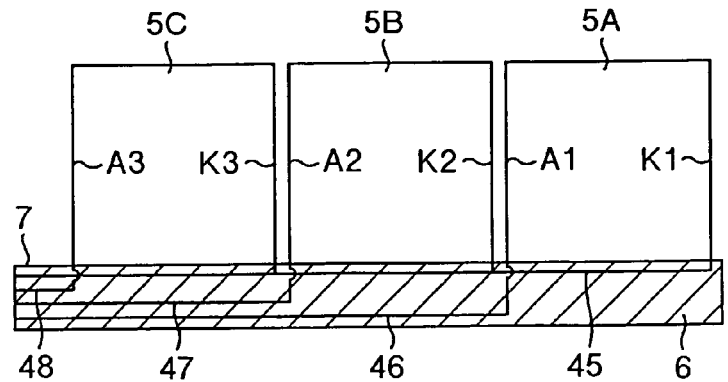
FIG. 6 is a sectional view of the detector support member in the radius direction of the detector unit in FIG. 5.
Figure 10:
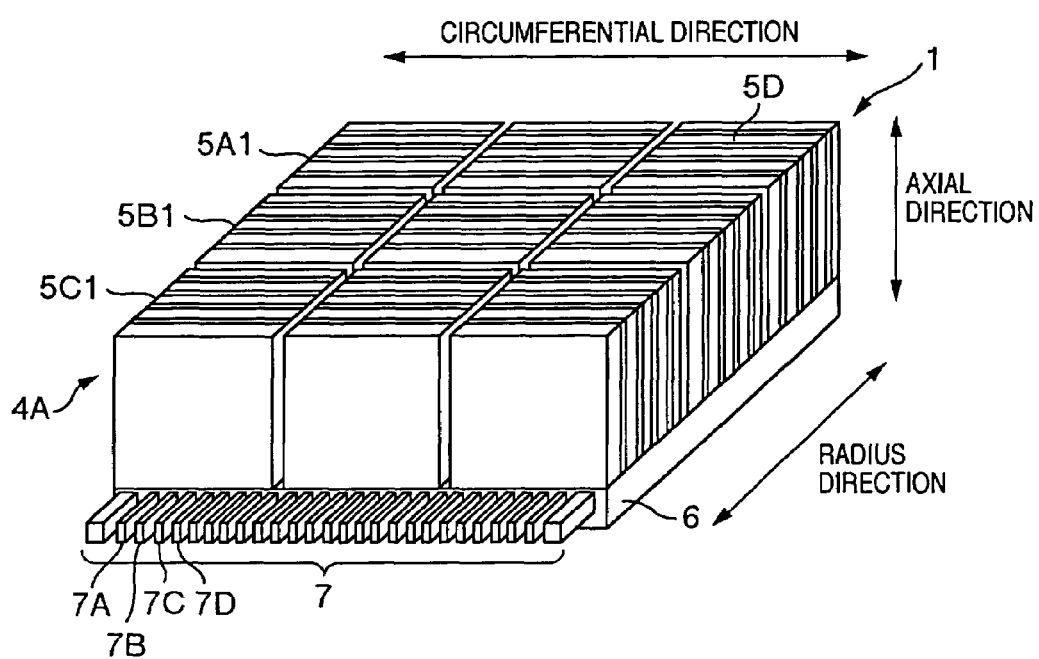
FIG. 10 is a perspective view of a detector unit applied to a radiological imaging apparatus according to Embodiment 2 which is another embodiment of the present invention.
Figure 12:
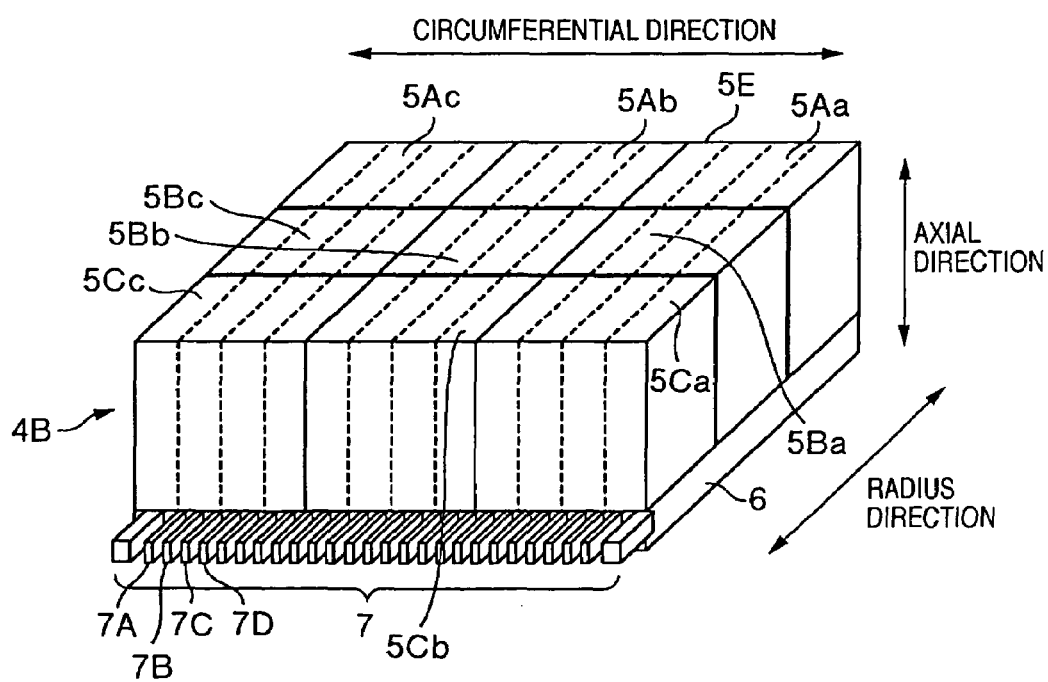
FIG. 12 is a perspective view of a detector unit applied to a radiological imaging apparatus according to Embodiment 3 which is a further embodiment of the present invention.

As shown in FIG. 5 and FIG. 6, the detector unit 4 has a structure in which a plurality (e.g., 9) of radiation detectors 5 are arranged on one side of the support substrate 6 and a connector section 7 is attached to the support substrate 6. Nine radiation detectors 5 are arranged in 3 rows and 3 columns on the support substrate 6. The "circumferential direction" shown in FIG. 4 refers to the circumferential direction of the detector support member 8, the "axial direction" refers to the axial direction of the detector support member 8 and the "radius direction" refers to the "radius direction of the detector support member 8 (the same applies to FIG. 10 and FIG. 12). Cathode electrodes K1, K2 and K3 of one column of the three radiation detectors 5 arranged in the radius direction of the detector support member 8, that is, radiation detectors 5A, 5B and 5C are connected to a grounding wire 45. The grounding wire 45 is connected to a connector terminal 7D of the connector section 7. A wire 46 connected to an anode electrode A1 of the radiation detector 5A is connected to a connector terminal 7A. A wire 47 connected to an anode electrode A2 of the radiation detector 5B is connected to a connector terminal 7B of the connector section 7. Furthermore, a wire 48 connected to an anode electrode A3 of the radiation detector 5C is connected to a connector terminal 7C of the connector section 7. The radiation detectors 5 included in other two columns are likewise connected to the other connector terminals provided for the connector section 7. The grounding wire 45 and wires 46, 47 and 48 are all set in the support substrate 6. The many detector units 4 are set and held in the detector support section 23 by engaging their respective connector terminals such as the connector terminal 7A with the connector section 11 provided in the detector support section 23. The detector units 4 surround the through hole section 41 and many of them are arranged in the circumferential direction and axial direction of the through hole section 41. These detector units 4 are attached to the detector support section 23 in a detachable manner.

The casing 3 is attached to the detector support section 23 so as to cover the detector units 4 (FIG. 4). Furthermore, the casing 3 extends in the horizontal direction and forms the hole section (through hole section) 41 into which the bed 20 is inserted during an inspection (FIG. 1).

With the arrangement of these detector units 4, many radiation detectors (e.g., 10,000 in total) 5 are arranged in the casing 3 on the inner side of the ring-shaped detector support member 8. These radiation detectors 5 are arranged in the radius direction of the detector support member 8 in multilayers (e.g., three layers) and also arranged in the axial direction of the detector support member 8 over a plurality of columns. The three radiation detectors 5 (radiation detectors 5A) located farthest from the connector section 7 of the radiation detectors 5 arranged in the respective detector units 4 are located closest to the central axis of the through hole section 41 and are called "first layer radiation detectors." The three radiation detectors 5 (radiation detectors 5C) located closest to the connector section 7 are located farthest from the central axis of the through hole section 41 and are called "third layer radiation detectors." The three radiation detectors 5 (radiation detectors 5B) located between the first layer and third layer in the detector unit 4 are called "second layer radiation detectors."

The radiation detection apparatus 43 includes the aforementioned many radiation detection units 4. The radiation detection apparatus 43 includes many radiation detectors 5 arranged in the radius direction of the detector support member 8 from the first layer to the third layer and arranged in the axial direction of the detector support member 8.

Examples of typical radiation detectors include a semiconductor radiation detector and scintillator. For the scintillator, a photoelectron multiplier, etc., needs to be arranged behind a crystal (BGO, NaI, etc.) which is a radiation detection section, and therefore it is unsuitable for a multilayer arrangement (e.g., three layers as described above). Since the semiconductor radiation detector requires no photoelectron multiplier, etc., it is suitable for a multilayer arrangement. In this embodiment, semiconductor radiation detectors are used for the radiation detectors 5 and a 5 mm cube which is a detection section is made of cadmium telluride (CdTe). The detection section may also be made of gallium arsenide (GaAs) or cadmium zinc telluride (CZT).

The signal processing apparatus 40 includes a signal discriminator 27, γ-ray discriminator 32 and the coincidence counter 34. One signal discriminator 27 is provided for each radiation detector 5 on the first layer. Furthermore, one γ-ray discriminator 32 is provided for each radiation detector 5 on the second layer and the third layer respectively. These three signal discriminators 27 and six γ-ray discriminators 32 are set on one substrate 26. A signal discrimination unit 25 is made up of the three signal discriminators 27 and six γ-ray discriminators 32 set on one substrate 26. The substrate 26 is attached to a unit support member 66. Each signal discrimination unit 25 provided for every detector unit 4 is attached to the unit support member 66 arranged in a signal discrimination unit housing space 44 as shown in FIG. 4. The unit support member 66 is attached to the detector support member 23. The signal discrimination unit 25 is set in the unit support member 66 and is thereby supported to the detector support member 8. It is also possible to attach the substrate 26 directly to the detector support member 23 as the support substrate without using the unit support member 66.

Figure 7:
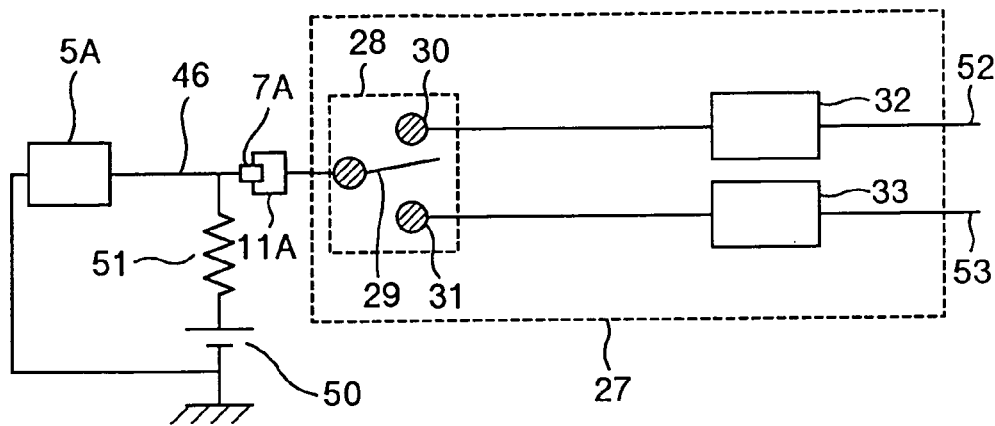
FIG. 7 shows a detailed structure of the signal discriminator in FIG. 1.

As shown in FIG. 7, the signal discriminator 27 includes a changeover switch 28, a γ-ray discriminator 32 and an X-ray signal processing apparatus 33. The changeover switch 28 includes a movable terminal 29 and fixed terminals 30 and 31. The γ-ray discriminator 32 is connected to the fixed terminal 30 and the X-ray signal processing apparatus 33 is connected to the fixed terminal 31. The connector terminal 7A connected to the first layer radiation detector 5A has contact with a connector terminal 11A provided for the connector section 11 through the engagement of the connector section 7 with the connector section 11. The movable terminal 29 is connected to the connector terminal 11A through a wire 49. The wire 49 is set in the unit support member 66. The minus terminal of a power supply 50 is connected to the wire 46 and the plus terminal of the power supply 50 is connected to the radiation detector 5A. The γ-ray discriminators 32 in all the signal discriminators 27 are connected to the coincidence counter 34 through a wire 52. On the other hand, the X-ray signal processing apparatuses 33 in all the signal discriminators 27 are connected to the computer 36 through a wire 53.

Three of the six γ-ray discriminators 32 other than the signal discriminator 27 provided in the signal discrimination unit 25 are connected to a connector terminal 11B of the connector section 11 (not shown) through a wire 54. The connector terminal 11B contacts the connector terminal 7B to which the second layer radiation detectors 5B are connected. The remaining three γ-ray discriminators 32 are connected to a connector terminal 11C (not shown) of the connector section 11 through another wire 54. The connector terminal 11B contacts the connector terminal 7C to which the third layer radiation detectors 5C are connected. The six γ-ray discriminators 32 other than the signal discriminator 27 are each connected to the coincidence counter 34 through a wire 55. FIG. 1 shows the signal discrimination unit 25 and wires 54 and 56 outside the detector support member 8 and this is intended to make the wiring connection states of the signal discriminator 27 and γ-ray discriminators 32 provided for the signal discrimination unit 25 easy to understand. The signal discrimination unit 25 is actually set in the detector support member 8 as shown in FIG. 3 and FIG. 4 and the wires 52, 53 and 55 are drawn out of the detector support member 8.

Before specifically explaining the radiological inspection in this embodiment, the principle of radiation detection of this embodiment will be explained. Data of an X-ray CT image (tomographic image including an image of internal organs and bones of an examinee obtained through X-ray CT) is created by irradiating X-rays radiated from the X-ray source onto an examinee in a specific direction for a predetermined time and repeating an operation of detecting (scanning) X-rays that have passed through the body using radiation detectors and based on the intensity of X-rays detected by a plurality of radiation detectors. In order to obtain accurate X-ray CT image data, it is preferable not to allow γ-rays emitted from the inside of the examinee caused by PET radiopharmaceutical to enter the radiation detectors which are detecting X-rays during an X-ray CT inspection. With regard to one radiation detector, if the time of X-ray irradiation onto the examinee is shortened in accordance with a rate of incidence of γ-rays, influences of γ-rays can be ignored, and therefore this system is designed to shorten the time of X-ray irradiation onto the examinee. To calculate the X-ray irradiation time T, a rate of incidence of γ-rays on one radiation detector is considered first. Suppose radioactivity in the body based on PET radiopharmaceutical administered to the examinee in a PET inspection is N (Bq), rate of generated γ-rays passing through the body is A, the rate of incidence calculated from the solid angle of one radiation detector is B and sensitivity of the detection element is C. Then, rate α (counts/sec) of γ-rays detected by one radiation detector is given by Expression (1).

$$\alpha = 2NABC \quad (1)$$

In Expression (1), coefficient "2" means that a pair (two) of γ-rays are emitted for annihilation of one positron. The probability W that γ-rays are detected by one detection element within the irradiation time T is given by Expression (2).

$$W = 1 - \exp(-T\alpha) \quad (2)$$

By determining the irradiation time T so that the value of W in Expression (2) is reduced, the influence of γ-rays incident on one radiation detector is reduced to a level as small as negligible during an X-ray CT inspection.

An example of the X-ray irradiation time T will be explained below. A specific X-ray irradiation time T was calculated based on Expressions (1) and (2). The intensity of radiation in the body caused by PET radiopharmaceutical administered to the examinee in a PET inspection is a maximum of approximately 370 MBq (N=370 MBq) and the rate of passage A of γ-rays through the body is on the order of 0.6 (A=0.6) when the body of the examinee is assumed to be water having a radius of 15 cm. For example, assuming a case where a radiation detector having a size of 5 mm per side is arranged in the shape of a ring having a radius of 50 cm, the rate of incidence B calculated from the solid angle of one radiation detector is $8\times10^{-8}$ ($B=8\times10^{-8}$). Furthermore, detection sensitivity C of the radiation detector is a maximum of approximately 0.6 ($C=0.6$) when a semiconductor radiation detector is used. From these values, the γ-ray detection rate α of one radiation detector is on the order of 2000 (counts/sec). Suppose the X-ray irradiation time T is 1.5 μsec, for example. Then, the probability W that one radiation detector will detect γ-rays during X-ray detection is 0.003 and most of these γ-rays can be ignored. When radioactivity in the body is 370 MBq or less, if the X-ray irradiation time is 1.5 μsec or less, $W<0.003$, that is, the probability W of γ-ray detection is 0.3% or less, which is negligible.

An X-ray CT inspection and a PET inspection in this embodiment where the above described principle is applied and the image pickup apparatus 2B is used will be explained more specifically.

An X-ray CT inspection and a PET inspection in this embodiment will be explained. PET radiopharmaceutical is administered to the examinee 42 using a method like injection in such a way that radioactivity in the body becomes 370 MBq. Then, the examinee 42 waits for a predetermined time until the PET radiopharmaceutical is spread in the body of the examinee 42, concentrated on an affected area (e.g., affected area of cancer) and image pickup is possible. PET radiopharmaceutical is selected according to the affected area to be inspected. After the lapse of the predetermined time, the bed 20 on which the examinee 42 lies is inserted into the through hole section 41 of the image pickup apparatus 2 together with the examinee 42. An X-ray CT inspection and a PET inspection are carried out using the image pickup apparatus 2. The examinee 42 with the PET radiopharmaceutical administered is inserted into the through hole section 41, a voltage is applied from the power supply 50 to the respective radiation detectors 5 and then the radiation detectors 5 detect γ-rays emitted from the examinee 42. That is, a PET inspection is started. After the PET inspection is started, an X-ray CT inspection is started.

The X-ray CT inspection will be explained. When the X-ray CT inspection is started, the drive apparatus control apparatus 21 outputs a drive start signal and closes the breaker (hereinafter referred to as "motor breaker") connected to the motor of the X-ray source drive apparatus 15 and connected to the power supply. The torque of the motor is transmitted to the pinion through the deceleration mechanism and the X-ray source apparatus 14, that is, the X-ray source 17 moves along the guide rail 12 in the circumferential direction. The X-ray source 17 moves around the examinee 42 at a set speed while being inserted in the through hole section 41. When the X-ray CT inspection is completed, the drive apparatus control apparatus 21 outputs a drive stop signal and opens the motor breaker. This stops the movement of the X-ray source 17 in the circumferential direction. In this embodiment, all the radiation detectors 5 move neither in the circumferential direction nor in the axial direction of the through hole section 41. The drive apparatus control apparatus 21 and X-ray source control apparatus 22 are set in the detector support member 8. A publicly known technology is applied to transmission of a control signal from the drive apparatus control apparatus 21 and X-ray source control apparatus 22 to the moving X-ray source apparatus 14 without interfering with the movement of the X-ray source apparatus 14.

The X-ray source control apparatus 22 controls the time of radiation of X-rays from the X-ray source 17. That is, the X-ray source control apparatus 22 outputs X-ray generation signals and X-ray stop signals repeatedly. The first X-ray generation signal is outputted based on the input of the above drive start signal to the X-ray source control apparatus 22. In response to the output of an X-ray generation signal, the breaker provided between the anode (or cathode) of the X-ray tube of the X-ray source 17 and the power supply (hereinafter referred to as "X-ray source breaker", not shown) is closed, an X-ray stop signal is outputted after a lapse of a first set time, the X-ray source breaker is opened and the X-ray source breaker is closed after a lapse of a second set time, and this control is repeated. Between the anode and cathode, a voltage is applied during the first set time, but no voltage is applied during the second set time. With such control by the X-ray source control apparatus 22, pulse-shaped 80 keV X-rays are radiated from the X-ray tube. An irradiation time T which is the first set time is set, for example, to 1 μsec so that the probability of detection of γ-rays at the radiation detector 5 can be ignored. The second set time is a time T0 during which the X-ray source 17 moves between one radiation detector 5 and another radiation detector 5 which is adjacent thereto in the circumferential direction and is determined by the moving speed of the X-ray source 17 in the circumferential direction of the guide rail 12. The first and second set times are stored in the X-ray source control apparatus 22.

In response to repeated outputs of X-ray stop signals and X-ray generation signals, the X-ray source 17 radiates X-rays during the first set time, that is, for 1 μsec and stops radiation of X-rays during the second set time. This radiation and stop of X-rays are repeated during a period during which the X-ray source 17 is moving in the circumferential direction.

The X-rays 57 radiated from the X-ray source 17 are irradiated onto the examinee 42 in a fan-beam shape. The examinee 42 receives irradiation of X-rays 57 as the X-ray source 17 moves in the circumferential direction. The X-rays 57 which have passed through the examinee 42 (e.g., X-rays that have passed through the affected area 56) are detected by a plurality of radiation detectors 5 located in the circumferential direction centered on the radiation detector 5 located at the position 180° from the X-ray source 17 relative to the central axis of the through hole section 41. These radiation detectors 5 output the detection signals of the X-rays 57. These X-ray detection signals are inputted to their respective signal discriminators 27 through the corresponding wires 49. The radiation detectors 5 that detect the above described X-rays are referred to as first radiation detectors 5 for the purpose of convenience.

From the affected area (affected area of cancer) of the examinee 42 on the bed 16, γ-rays 58 of 511 keV caused by PET radiopharmaceutical are emitted. The radiation detectors 5 other than the first radiation detectors 5 detect the γ-rays 58 and output γ-ray detection signals. The radiation detectors 5 detecting γ-rays are called "second radiation detectors 5" for the purpose of convenience. The γ-ray detection signals outputted from the second radiation detectors 5 located on the first layer out of the second radiation detectors are inputted to their respective signal discriminators 27 through the corresponding wires 49 and the γ-ray detection signals outputted from the second radiation detectors 5 located on the second layer and third layer are inputted to their respective γ-ray discriminators 32 through the corresponding wires 54. Only the radiation detectors 5 located on the first layer are connected to the signal discriminator 61 having the X-ray signal processing apparatus 33. This is because energy of the X-rays is 80 keV and most (90% or more) of the X-rays that have passed through the examinee 42 are detected by the first layer radiation detectors 5.

In the signal discriminators 27, the γ-ray detection signals outputted from the first layer second radiation detectors 5 are transmitted to the γ-ray discriminators 32 and the X-ray detection signals outputted from the first radiation detectors 5 are transmitted to the X-ray signal processing apparatus 33. Such transmission of each detection signal is performed according to the changeover operation of the changeover switch 28 of the signal discriminator 27. The changeover operation for connecting the movable terminal 29 of the changeover switch 28 to the fixed terminal 30 or fixed terminal 31 is performed based on the changeover control signal which is the output of the drive apparatus control apparatus 21. During an X-ray CT inspection, the drive apparatus control apparatus 22 selects the first radiation detectors 5 of the first layer radiation detectors 5 and connects the movable terminal 29 of the signal discriminators 27 connected to these first radiation detector 5 to the fixed terminal 31.

The selection of the first radiation detectors 5 will be explained. The motor in the X-ray source drive apparatus 15 is connected with an encoder (not shown). The drive apparatus control apparatus 22 receives a detection signal of the encoder and calculates the position of the X-ray source drive apparatus 15 in the circumferential direction of the detector support member 8 (through hole section 41), that is, the position of the X-ray source 17 and selects the radiation detector 5 located 180° opposite to the position of the X-ray source 17 using the stored data of the position of each radiation detector 5. The X-rays 57 radiated from the X-ray source 17 has a certain width in the circumferential direction of the guide rail 12, and therefore there are a plurality of radiation detectors 5 in the circumferential direction other than the selected radiation detectors 5 which detect the X-rays 57 that have passed through the examinee 42. The drive apparatus control apparatus 22 selects those plurality of radiation detectors 5, too. These radiation detectors 5 are the first radiation detectors 5. The first radiation detectors 5 also change depending on the movement of the X-ray source 17 in the circumferential direction. As the X-ray source 17 moves in the circumferential direction, the first radiation detectors 5 also seem to move in the circumferential direction. When the drive apparatus control apparatus 22 selects other radiation detectors 5 as the X-ray source 17 moves in the circumferential direction, the movable terminal 29 connected to the radiation detectors 5 which become the new first radiation detectors 5 is connected to the fixed terminal 31. The movable terminal 29 connected to the radiation detectors 5 which are no longer the first radiation detectors 5 as the X-ray source 17 moves in the circumferential direction is connected to the fixed terminal 30 by the drive apparatus control apparatus 22. According to the positional relationship with the X-ray source 17, the first layer radiation detectors 5 sometimes become the first radiation detectors 5 and sometimes become the second radiation detectors 5. For this reason, one radiation detector 5 on the first layer outputs both an X-ray detection signal and γ-ray detection signal with a time shift in between.

The first radiation detectors 5 receive irradiation from the X-ray source 17 for 1 μsec which is the first set time and detect X-rays which have passed through the examinee 42. The probability that the first radiation detectors 5 detect γ-rays emitted from the examinee 42 for 1 μsec is as small as negligible as described above. Many γ-rays 58 generated at the affected area 56 of the examinee 42 caused by PET radiopharmaceutical are not emitted in a specific direction but emitted in all directions. These γ-rays 58 form pairs and are emitted in directions opposite to each other (180°±0.6°) as described above and detected by either one of the second radiation detectors 5.

The signal processing of the signal discriminators 27 when the X-ray detection signals and γ-ray detection signals outputted from the first layer radiation detectors 5 are inputted will be explained. As described above, the X-ray detection signals outputted from the first layer radiation detectors 5 are inputted to the X-ray signal processing apparatus 33. The X-ray signal processing apparatus 33 integrates the input X-ray detection signals using an integration apparatus and outputs the X-ray detection signal integrated value, that is, information on the intensity of the measured X-rays. The intensity information of the X-ray detection signals is transmitted to the computer 26 through the wire 53 and stored in the storage apparatus 37.

The γ-ray detection signals outputted from the first layer second radiation detectors 5 are inputted to the γ-ray discriminators 32 by an action of the changeover switch 28. By annihilation of positrons emitted from PET radiopharmaceutical, energy of γ-rays emitted from the affected area 56 is 511 keV. However, when γ-rays are scattered in the body of the examinee 42, the energy falls below 511 keV. To remove scattered γ-rays, the γ-ray discriminators 32 is provided with a filter (not shown) which allows γ-ray detection signals having energy equal to or greater than an energy set value of 400 keV which is lower than 511 keV to pass. This filter receives the γ-ray detection signals outputted from the fixed terminal 30. Here, 400 keV was used as the energy set value because variations of the γ-ray detection signals produces when γ-rays of 511 keV enter the radiation detectors 5 are taken into consideration. The γ-ray discriminators 32 generate a pulse signal having predetermined energy when γ-ray detection signals having energy equal to or greater than the energy set value (400 keV) are inputted. The γ-ray discriminator 32 is a γ-ray detection signal processing apparatus and gives the pulse signal to be output time information and position information indicating the position of the radiation detector 5 connected to the γ-ray discriminator 32. The time information is either the information when γ-ray detection signals are inputted to the γ-ray discriminator 32 or information when a pulse signal is outputted from the γ-ray discriminator 32.

All the second layer and third layer radiation detectors 5 are the second radiation detectors. The γ-ray discriminators 32 connected to these second layer and third layer radiation detectors 5 through the wire 54 also exhibits the same functions as those of the γ-ray discriminators 32 in the above described signal discriminators 27.

The coincidence counter 34 receives pulse signals outputted from all the γ-ray discriminators 32. The coincidence counter 34 performs simultaneous counting using pulse signals for respective γ-ray detection signals outputted from the two second radiation detectors 5 which have detected each γ-ray 58 of the γ-ray pair (a pair of the second radiation detectors which exist at substantially 180° (more precisely 180°±0.6°) different positions centered on the central axis of the through hole section 41) and calculates the count rate (γ-ray count information) corresponding to their respective γ-ray detection signals. The coincidence counter 34 decides whether each pulse signal corresponds to the respective γ-ray detection signals of the γ-ray pair or not based on the time information given to each pulse signal. That is, if the difference between two time information pieces is within a set time (e.g., 10 nsec), the coincidence counter 34 decides that the pulse signal corresponds to a pair of γ-rays 58 generated by annihilation of one positron. Furthermore, the coincidence counter 34 creates data from the position information given to those pulse signals as the position of the corresponding pair of second radiation detectors 5, that is, the position information of each γ-ray detection point. The coincidence counter 34 outputs the count rate information corresponding to each γ-ray detection signal and the position information of the two detection points at which the γ-ray pair is detected. The count rate and position information are transmitted to the computer 36 and stored in the storage apparatus 37.

Figure 8:
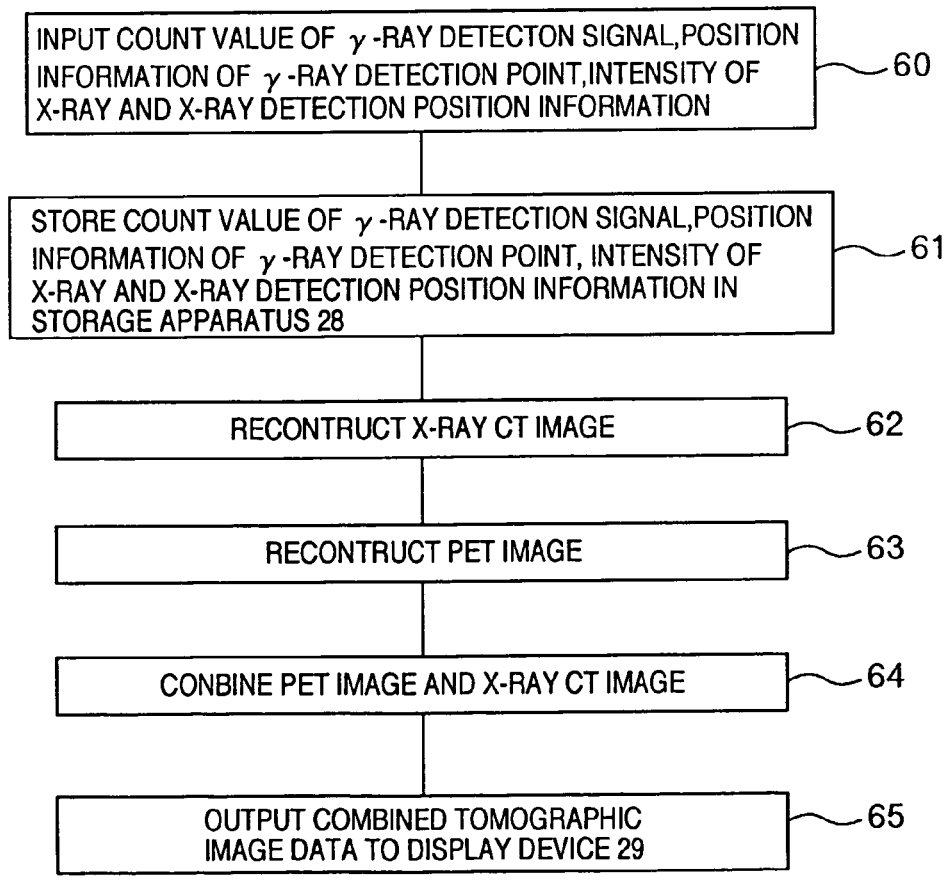
FIG. 8 illustrates a procedure for creating a tomographic image executed by the computer in FIG. 1.

The computer 36 carries out processing based on the processing procedure in steps 60 to 65 shown in FIG. 8. The computer 36 that carries out such processing is a tomography creation section that creates first tomographic image information using first information (more specifically, γ-ray count information and position information of the γ-ray detection point), creates second tomographic image information (more specifically, X-ray CT image data) using second information (more specifically, X-ray intensity information and X-ray detection position information) and third tomographic image information (more specifically, combined tomography data) including the first tomographic image information and second tomographic image information using those tomographic image information pieces. The count rate information of the γ-ray detection signal counted by the coincidence counter 34, position information of the γ-ray detection signal outputted from the coincidence counter 34, X-ray intensity information outputted from the X-ray signal processing apparatus 33 and X-ray detection position information given to the X-ray intensity are inputted (step 60). The inputted count rate information of the γ-ray detection signal, position information of the γ-ray detection point, X-ray intensity information and X-ray detection position information are stored in the storage apparatus 37 (step 61).

The tomographic image of the cross section (hereinafter the "cross section" will refer to the cross section when the examinee is in standing posture) of the examinee 42 is reconstructed using the X-ray intensity information and X-ray detection position information (step 62). The reconstructed tomographic image is called an "X-ray CT image." Specific processing of reconstruction of this tomographic image will be explained. First, the attenuation rate of X-rays in each voxel in the body of the examinee 42 is calculated using the X-ray intensity information. This attenuation rate is stored in the storage apparatus 37. To reconstruct the X-ray CT image, the linear attenuation coefficient in the body of the examinee 42 between the position of the X-ray source 17 and the position of the radiation detector 5 which has detected the X-rays (obtained from the X-ray detection position information) is calculated using the attenuation rate of the X-ray detection signal read from the storage apparatus 37. The position of the X-ray source 17 during movement detected by the encoder is given to the X-ray intensity information by each X-ray signal processing apparatus 33 and transmitted to the computer 36. The CT value of each voxel is calculated based on the value of the linear attenuation coefficient obtained by the filtered back projection method using the linear attenuation coefficient. The data of the X-ray CT image is obtained using those CT values and stored in the storage apparatus 37. In step 62, the X-ray CT image on the cross section that passes through the affected area where PET radiopharmaceutical is concentrated is also reconstructed.

The tomographic image of the cross section of the examinee 42 including the affected area (e.g., the affected area of cancer) is reconstructed using the count rate of the γ-ray detection signal at the corresponding position (step 63). The tomographic image reconstructed using the count rate of the γ-ray detection signal is called a "PET image". This processing will be explained in detail. Using the count rate of the γ-ray detection signal read from the storage device 37, the number of γ-ray pairs generated (the number of γ-ray pairs generated according to annihilation of a plurality of positrons) in the body between the semiconductor devices of a pair of the second radiation detectors 5 (specified by position information of the γ-ray detection point) is calculated. Using this number of γ-ray pairs generated, a γ-ray pair generation density of each voxel is calculated according to the filtered back projection method. PET image data can be obtained based on this γ-ray pair generation density. This PET image data is stored in the storage device 37.

The PET image data is combined with the X-ray CT image data to obtain combined tomographic data including both data pieces and stored in the storage device 37 (step 64). The PET image data at the position of the affected area and X-ray CT image data at the position are combined to obtain combined tomographic image data on the cross section of the examinee 42 at the position of the affected area. The combination of the PET image data and X-ray CT image data can be performed easily and accurately by aligning the central axis of the through hole section 41 in both image data pieces. That is, the PET image data and X-ray CT image data are created based on the detection signals outputted from the shared radiation detector 5, and therefore alignment can be performed accurately as described above. The combined tomographic data is called from the storage device 37 and output to the display device 38 (step 65) and displayed on the display device 38. The combined tomographic image displayed on the display device 38 includes an X-ray CT image, and therefore it is possible to easily check the position in the body of the examinee 42 of the affected area in the PET image. That is, since the X-ray CT image includes images of internal organs and bones, doctors can identify the position of the affected area (e.g., the affected area of cancer) from the relationship with the internal organs or bones.

Figure 9A:
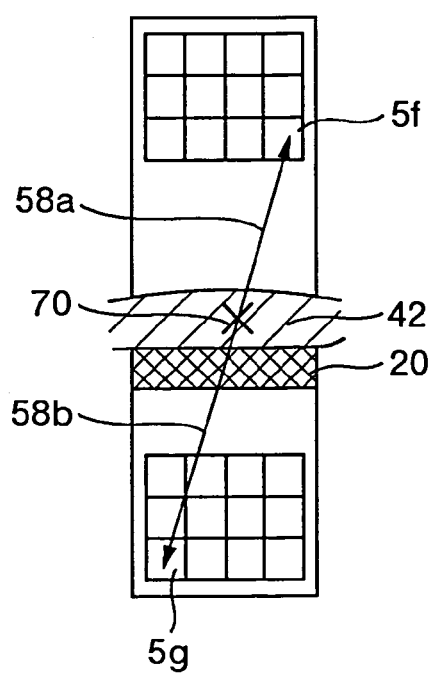
FIGS. 9A and 9B illustrate a state of γ-ray detection in the embodiment shown in FIG. 1.
Figure 9B:
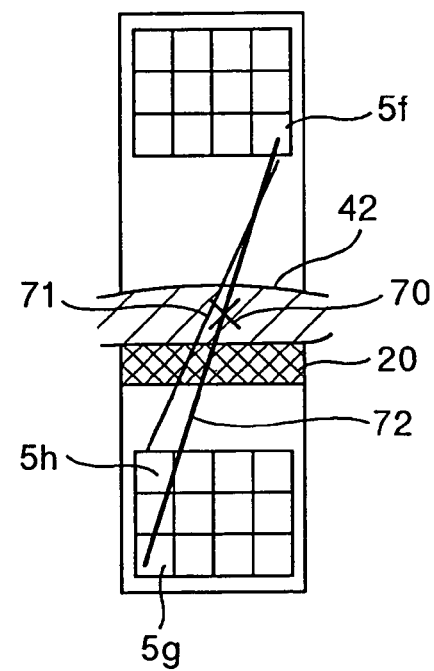

The radiological imaging apparatus 1 comprises a plurality of radiation detectors 5 multilayered in the radius direction of the through hole section 41 (FIG. 1 to FIG. 4) and this multilayer arrangement can bring out the following new function. For example, suppose a case where two γ-rays 58*a* and 58*b* emitted from a point of γ-ray pair generation 70 (in the affected area 56) in the body of the examinee 42 as shown in FIG. 9A enter radiation detectors 5*f* and 5*g*. It is unknown at which position in the radiation detector the γ-rays have attenuated, and therefore the conventional method considers a line connecting the end positions of the pair of the radiation detectors 5*f* and 5*h*, that is, a line 71 shown in FIG. 9B as a detection line. However, since the radiological imaging apparatus 1 adopts the multilayer arrangement of the radiation detectors 5 in the radius direction of the through hole section 41, it is possible to obtain a γ-ray detection signal of the radiation detector 5*g* located outside in the radius direction and consider a line 72 connecting the radiation detector 5*f* and radiation detector 5*g* as a detection line. That is, it is possible to grasp the attenuation position in the depth direction of the radiation detectors 5 which have been unknown in the conventional example. As a result, the detection line 72 precisely passes through the position at which a pair of γ-rays are generated and therefore the accuracy of the image improves. As a result, the detection line is brought closer to the actual point of generation of the pair of γ-rays and accuracy of measured data improves.

In this embodiment, the radiation detection apparatus 43 comprises a plurality of radiation detectors 5 which output both X-ray detection signals and γ-ray detection signals, and therefore the radiation detection apparatus 43 functions as a γ-ray detection section as well as an X-ray detection section. That is, the radiation detection apparatus 43 has both functions of the γ-ray detection section and X-ray detection section. In this embodiment, the X-ray detection section is positioned in an area formed between one end of the γ-ray detection section and the other end of the γ-ray detection section in the longitudinal direction of the bed 20. Furthermore, the radiation detection apparatus 43 is an X-ray detection section that detects X-ray 57 which is irradiated from the X-ray source 17 and passes through the examinee 42 and outputs a detection signal of this X-ray 57 and at the same time is a γ-ray detection section that detects a γ-ray 58 emitted caused by PET radiopharmaceutical from the area (affected area 56) through which the X-ray 57 in the examinee 42 passes at the position of the examinee 42 irradiated with the X-ray 57 and outputs a detection signal of this γ-ray 58.

This embodiment can attain the effects described below.
(1) In this embodiment, a plurality of detection units 4 are attached to the detector support member 8 through the connector section, and therefore these detection units 4, or more specifically, many radiation detectors 5 can be attached in a short time. This makes it possible to shorten the time for manufacturing the image pickup apparatus 2, that is, the radiological imaging apparatus 1.
(2) Since the detection units 4 are attached to the detector support member 8 through the connector section in a detachable manner, when a radiation detector 5 has trouble, the detection unit 4 including the radiation detector 5 in trouble can be easily removed from the detector support member 8. Furthermore, a new detection unit 4 can be easily attached to the detector support member 8 at the position of the removed detector unit. Thus, this embodiment allows a damaged radiation detector 5 to be replaced easily.
(3) This embodiment arranges the plurality of radiation detectors 5 not only in the axial direction and circumferential direction of the through hole section 41 (detector support member 8) but also in the radius direction, and can thereby obtain γ-ray detection signals at the positions subdivided in the radius direction of the through hole section 41 without reducing signal transmission substances as in the case of conventional radiation detectors used for a PET inspection. Thus, this embodiment can obtain precise information on the position that γ-rays reach in the radius direction of the through hole section 41 (position information of the radiation detectors 5 which have output γ-ray detection signals). In a conventional PET inspection, one radiation detector is placed in the radius direction of the through hole section 41, a reflector is placed inside this radiation detector and the information on the position that γ-rays have reached in the radius direction of the through hole section 41 is obtained according to a pattern with which the signal transmission substance reaches the photoelectron multiplier. At this moment, part of the signal transmission substance attenuates in the radiation detector because of the reflector and is reflected to the outside of the radiation detector, which reduces the signal transmission substance and reduces energy resolution.
(4) This embodiment arranges a plurality of independent radiation detectors 5 in the radius direction of the through hole section 41, and can thereby use all the signal transmission substance of the radiation detectors 5 for detection of γ-rays and improve energy resolution of the radiation detectors 5. Use of the radiation detectors 5 with high energy resolution for a PET inspection makes it possible to distinguish γ-rays whose energy has attenuated due to scattering from un-scattered γ-rays having energy of 511 keV. As a result, it is possible to remove more scattered radiation through a filter of the γ-ray discriminator 32.
(5) This embodiment can acquire precise information on the position that γ-rays reach in the radius direction of the through hole section 41 without reducing the number of signal transmission substances in the radiation detectors, and therefore using the precise information on the position that γ-rays reach improves the accuracy of tomography, eliminates the need for the reflector for the radiation detectors and can thereby prevent the reduction of the signal transmission substances, improve the energy resolution and suppress influences of scattered rays on the reconstruction of the tomography. As a result, this embodiment can improve the accuracy of tomography, that is, diagnostic accuracy of a PET inspection.
(6) This embodiment uses semiconductor radiation detectors as the radiation detectors 5, and can thereby arrange a plurality of radiation detectors 5 in the radius direction of the through hole section 41 and such an arrangement of the plurality of radiation detectors 5 does not increase the size of the image pickup apparatus 2.
(7) Using semiconductor radiation detectors for the radiation detectors 5, this embodiment eliminates the need for any photoelectron multiplier which is required for radiation detectors using a scintillator and can thereby reduce the size of the image pickup apparatus 2.
(8) Arranging the radiation detectors 5 which are semiconductor radiation detectors on the support substrate, this embodiment allows the radiation detectors 5 to be arranged densely. Allowing especially radiation detectors 5 with small detector widths to be arranged densely in the circumferential direction of the through hole section 41, this embodiment can realize high resolution (small image voxel size) of the tomographic image.
(9) Adopting the configuration of arranging the radiation detectors 5 on the support substrate 6, this embodiment allows the radiation detectors 5 to be arranged densely. This allows an arrangement of a plurality of radiation detectors 5 in the radius direction of the through hole section 41 in particular and realizes high detection efficiency. Moreover, since the radiation detectors 5 in the radius direction can detect γ-rays independently, the resolution in the radius direction improves. In a 3D (three-dimensional) PET inspection in particular, there may be a case where γ-rays enter the radiation detectors 5 diagonally, but with an improvement of the resolution in the radius direction, it is possible to grasp the direction of incidence of γ-rays accurately. This can improve the quality of PET images obtained.
(10) According to this embodiment, wires connected to the radiation detectors 5 are arranged in the support substrate 6, and therefore it is possible to shorten the distance between the radiation detectors 5 in the circumferential direction and axial direction of the through hole section 41. The shortening of the distance between the radiation detectors 5 reduces omissions in γ-ray detection and substantially increases the γ-ray detection efficiency. The substantial increase of γ-ray detection efficiency can shorten a PET inspection time.

(11) Using the radiation detectors 5 which have detected γ-rays as the radiation detectors 5 to detect X-rays, the radiological imaging apparatus 1 need not provide the radiation detectors 5 to detect X-rays and the radiation detectors 5 to detect γ-rays separately, and can thereby simplify the configuration and reduce the size of the apparatus. The radiation detectors 5 output both X-ray detection signals and γ-ray detection signals.

(12) In this embodiment, the X-ray detection section is positioned in an area formed between one end of the γ-ray detection section and the other end of the γ-ray detection section in the longitudinal direction of the bed 20, and therefore even when the examinee 42 moves during an inspection independently of the movement of the bed 20, it is possible to combine the information of the first tomographic image (PET image) created based on the first information obtained from a γ-ray detection signal outputted from the γ-ray detection section and the information of the second tomographic image (X-ray computer tomographic image) obtained from the X-ray detection signal outputted from the X-ray detection section and improve the accuracy of the created tomographic image of the examinee 42. Using the tomographic image can improve the accuracy of diagnosis of the examinee. More specifically, the position and size of the affected area of cancer can be recognized accurately. It is especially possible to diagnose cancer of lymph gland which is a small organ.

(13) As described above, according to this embodiment, the radiation detection apparatus 43 consists of a plurality of radiation detectors 5 which output both X-ray detection signals and γ-ray detection signals (detection of X-rays to obtain X-ray detection signals is performed using the radiation detectors 5 to detect γ-rays to obtain γ-ray detection signals) and therefore the radiation detection apparatus 43 is provided with both functions of the γ-ray detection section and X-ray detection section. The radiation detection apparatus 43 can be said to arrange the γ-ray detection section and X-ray detection section coaxially. For this reason, this embodiment can reconstruct the first tomographic image at the position of an affected area (where PET radiopharmaceutical is concentrated) including internal organs and bones of the examinee 42 and reconstruct the second tomographic image including the image of the affected area of the examinee 42 using the γ-ray detection signals which are other output signals of the radiation detectors 5. The data of the first tomographic image and data of the second tomographic image are reconstructed based on the output signals of the radiation detectors 5 which detect both transmitted X-rays and γ-rays, and therefore it is possible to combine the data of the first tomographic image and the data of the second tomographic image aligned with each other with high accuracy. In this way, it is possible to easily obtain an accurate tomographic image (combined tomographic image) including images of the affected area, internal organs and bones, etc. According to this combined tomographic image, it is possible to accurately identify the position of the affected area from the relationship with the internal organs or bones. For example, by aligning the data of the first tomographic image and the second tomographic image based on the central axis of the detector support member 8 (or through hole section 41) of the image pickup apparatus 2, it is possible to easily obtain image data combining both tomographic images.

(14) In this embodiment, the X-ray detection section detects X-rays 57 which have been radiated from the X-ray source 17 and pass through the affected area 56 of the examinee 42 and the γ-ray detection section detects γ-rays emitted caused by radiopharmaceutical from the area (affected area) in the body of the examinee 42 through which X-rays pass at the position of the examinee irradiated with the X-rays, and therefore it is possible to carry out an X-ray CT inspection and PET inspection at the same position without moving the examinee 42 with the bed 20. During both inspections, the X-ray detection section outputs a detection signal of X-rays that have passed through the affected area 56 of the examinee 42 and the γ-ray detection section outputs a detection signal of γ-rays emitted from the affected area 56. The first tomographic image data at the position of the affected area 56 obtained based on the X-ray detection signal is combined with the second tomographic image data at the position of the affected area obtained based on the γ-ray detection signal, and therefore even if the examinee 42 can no longer keep the same posture moves on the bed 20 during an inspection, it is possible to combine those tomographic image data pieces accurately. That is, this embodiment can obtain combined tomographic image data with a high degree of accuracy. Thus, using the combined tomographic image data (combined tomographic image) at the position of the affected area 56 displayed on the display device 38 can improve the accuracy of diagnosis of the affected area 56. Even when the affected area is located especially in a place where organs intercross, the combined tomographic image data obtained in this embodiment makes it possible to keep track of the position of the affected area appropriately and improve the accuracy of diagnosis of the affected area.

(15) According to this embodiment, using the X-ray source axial transport apparatus (e.g., axial transport arm 16), the X-ray source 17 can be transported in the axial direction of the radiation detector 5 during radiological inspection, and therefore an X-ray CT inspection can be carried out on the range of the inspection target while carrying out a PET inspection on the range of the inspection target without transporting the examinee 42 in the axial direction of the radiation detection apparatus 43. When an X-ray CT inspection is carried out on the range of the inspection target while moving the examinee 42 by transporting the bed 20 without moving the X-ray source 17 in the axial direction, the position of the area where PET radiopharmaceutical is concentrated also moves in the axial direction. This means that the position at which a γ-ray pair is generated is moved in the axial direction, resulting in increased noise when PET image data is created, failing to obtain accurate PET image data. In this embodiment, the position at which a γ-ray pair is generated is not moved in the axial direction, resulting in accurate PET image data and improved accuracy of combined tomographic image data.

(16) According to this embodiment, it is possible to detect a plurality of γ-ray pairs emitted from the examinee 42 using the radiation detectors 5 included in the radiation detection apparatus 43 and also detect X-rays which have been radiated from the X-ray source 17 moving in the circumferential direction and passed through the examinee 42. In this way, while the conventional art requires an image pickup apparatus for detecting X-rays and another image pickup apparatus for detecting γ-rays, this embodiment only requires a single image pickup apparatus to detect X-rays and γ-rays and simplifies the configuration of the radiological imaging apparatus capable of executing both X-ray CT inspection and PET inspection.

(17) This embodiment allows the common radiation detectors 5 to obtain X-ray detection signals necessary for creating a first tomographic image and γ-ray detection signals necessary for creating a second tomographic image, making it possible to drastically shorten the time required to inspect the examinee 42 (inspection time). In other words, it is possible to obtain X-ray detection signals necessary for creating a first tomographic image and γ-ray detection signals necessary for creating a second tomographic image in a short inspection time. This embodiment eliminates the need in the prior art for transporting the examinee 42 from one image pickup apparatus for detecting transmitting X-rays to another image pickup apparatus for detecting γ-rays, and therefore further contributes to a reduction of the inspection time of the examinee 42.

(18) This embodiment rotates the X-ray source 17 and moves the radiation detection apparatus 43 in neither the circumferential direction nor axial direction of the through hole section 41, can thereby reduce the capacity of the motor for rotating the X-ray source 17 compared to the motor necessary to move the radiation detection apparatus 43. Power consumption necessary for driving the motor of the latter can also be reduced compared to power consumption of the motor of the former.

(19) Since γ-ray detection signals are inputted to the X-ray signal processing apparatus 33, that is, the first signal processing apparatus is reduced drastically, it is possible to obtain an accurate first tomographic image data. Thus, using image data obtained by combining the first tomographic image data and second tomographic image data allows the position of the affected area to be known precisely.

(20) In this embodiment, the X-ray source 17 rotates inside the radiation detection apparatus 43, and therefore the inner diameter of the detector support member 8 increases and the number of radiation detectors 5 that can be provided in the circumferential direction inside the detector support member 8 can be increased. An increase in the number of radiation detectors 5 in the circumferential direction results in an improvement in sensitivity and resolution and improves the resolution of the tomographic image on the cross section of the examinee 42.

(21) Since the axial transport arm 16 and X-ray source 17 are located inside the radiation detection apparatus 43, they intercept γ-rays emitted from the examinee 42 during an X-ray CT inspection and the radiation detectors 5 located right behind them cannot detect the γ-rays, which may cause detection data necessary for creation of a PET image to be lost. However, since the X-ray source drive apparatus 15 rotates the X-ray source 17 and the axial transport arm 16 in the circumferential direction as described above, the loss of data substantially causes no problem. Especially, the rotational speed of the X-ray source 17, and the axial transport arm 16 is approximately 1 sec/1 slice, which is short enough when compared to a time required for a PET inspection which takes approximately a few minutes at the shortest. The loss of the data is therefore substantially no problem. Furthermore, when a PET inspection is carried out without any X-ray CT inspection, the X-ray source 17 is housed in the X-ray source drive apparatus 15 and therefore the X-ray source 17 and the axial transport arm 16 do not constitute obstacles to detection of γ-rays.

Moreover, the inspection time necessary to obtain an X-ray detection signal necessary to create an X-ray CT image is shorter than the inspection time necessary to obtain a γ-ray image pickup signal necessary to create a PET image. Thus, during an inspection time to obtain a γ-ray detection signal, X-rays are always irradiated from the X-ray source 17 onto the examinee 42 to obtain an X-ray detection signal and in this way even when the examinee 42 moves during an inspection, it is also possible to correct a data shift of the PET image caused by the movement of the examinee 42 from successive X-ray CT images obtained based on the X-ray detection signal.

The wires connected to the radiation detectors 5 are arranged inside the support substrate 6, but it is also possible to form a through hole in the support substrate 6, pass the wires from the side of the support substrate 6 on which the radiation detectors 5 are arranged through the through hole, pull the wires out of the opposite side and arrange the wires on the surface of the support substrate 6 on the side on which no radiation detectors 5 are arranged. In that case, it is also possible to form grooves on the surface of the side of the support substrate 6 on which no radiation detectors 5 are arranged and set the wires in the grooves. Furthermore, it is also possible to use a multilayer wire board as the support substrate and set wires inside the multilayer wiring board. Furthermore, use of the multilayer wiring board allows the radiation detectors 5 to be arranged on both sides of the multilayer wiring board.

(Embodiment 2)

Figure 11:
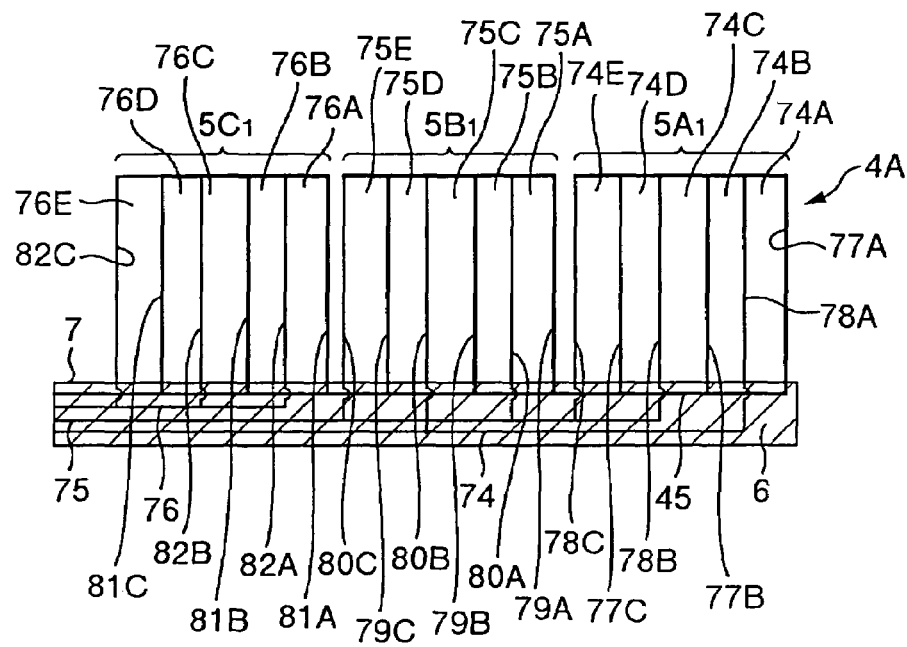
FIG. 11 is a sectional view of the detector support member in the radius direction of the detector unit in FIG. 10.

A radiological imaging apparatus according to Embodiment 2 which is another preferred embodiment of the present invention will be explained below. The radiological imaging apparatus in this embodiment only differs from the configuration of the radiological imaging apparatus 1 of Embodiment 1 in the configuration of the detector unit 4. A detector unit 4A used in this embodiment having a configuration different from that of the detector unit 4 used in Embodiment 1 will be explained with reference to FIG. 10 and FIG. 11.

The detector unit 4A consists of a plurality (e.g., 9) of radiation detectors 5D arranged in 3 rows and 3 columns on one side of a support substrate 6. Each radiation detector 5D is the same semiconductor radiation detector as the radiation detector 5 and three layers of the radiation detectors 5D are arranged in the radius direction of a detector support member 8. Of one column in the radius direction of the detector support member 8, a radiation detector $5A_1$, radiation detector $5B_1$ and radiation detector $5C_1$ are arranged on the first layer, second layer and third layer respectively.

The radiation detector $5A_1$ consists of five detection elements, that is, detection elements 74A, 74B, 74C, 74D and 74E. The detection elements 74A, 74B, 74C, 74D and 74E are arranged in that order from the inner side in the radius direction of the detector support member 8. The detection element 74A is arranged on the innermost side, while the detection element 74E is arranged on the outermost side. A cathode electrode 77A is provided on the inner side of the detection element 74A. The detection element 74A and detection element 74B are adjacent to each other with an anode electrode 78A sandwiched between the outer surface of the detection element 74A and the inner surface of the detection element 74B. The detection element 74B and detection element 74C are adjacent to each other with a cathode electrode 77B sandwiched between the outer surface of the detection element 74B and the inner surface of the detection element 74C. The detection element 74C and detection element 74D are adjacent to each other with an anode electrode 78B sandwiched between the outer surface of the detection element 74C and the inner surface of the detection element 74D. The detection element 74D and detection element 74E are adjacent to each other with a cathode electrode 77C sandwiched between the outer surface of the detection element 74D and the inner surface of the detection element 74E. An anode electrode 78C is provided on the outer surface of the detection element 74E.

The radiation detector $5B_1$ consists of five detection elements, that is, detection elements 75A, 75B, 75C, 75D and 75E. The detection elements 75A, 75B, 75C, 75D and 75E are arranged in that order from the inner side in the radius direction of the detector support member 8. The detection element 75A is arranged on the innermost side, while the detection element 75E is arranged on the outermost side. A cathode electrode 79A is provided on the inner side of the detection element 75A. The detection element 75A and detection element 75B are adjacent to each other with an anode electrode 80A sandwiched between the outer surface of the detection element 75A and the inner surface of the detection element 75B. The detection element 75B and detection element 75C are adjacent to each other with a cathode electrode 79B sandwiched between the outer surface of the detection element 75B and the inner surface of the detection element 75C. The detection element 75C and detection element 75D are adjacent to each other with an anode electrode 80B sandwiched between the outer surface of the detection element 75C and the inner surface of the detection element 75D. The detection element 75D and detection element 75E are adjacent to each other with a cathode electrode 79C sandwiched between the outer surface of the detection element 75D and the inner surface of the detection element 75E. An anode electrode 80C is provided on the outer surface of the detection element 75E.

The radiation detector $5C_1$ consists of five detection elements, that is, detection elements 76A, 76B, 76C, 76D and 76E. The detection elements 76A, 76B, 76C, 76D and 76E are arranged in that order from the inner side in the radius direction of the detector support member 8. The detection element 76A is arranged on the innermost side, while the detection element 76E is arranged on the outermost side. A cathode electrode 81A is provided on the inner side of the detection element 76A. The detection element 76A and detection element 76B are adjacent to each other with an anode electrode 82A sandwiched between the outer surface of the detection element 76A and the inner surface of the detection element 76B. The detection element 76B and detection element 76C are adjacent to each other with a cathode electrode 81B sandwiched between the outer surface of the detection element 76B and the inner surface of the detection element 76C. The detection element 76C and detection element 76D are adjacent to each other with an anode electrode 82B sandwiched between the outer surface of the detection element 76C and the inner surface of the detection element 76D. The detection element 76D and detection element 76E are adjacent to each other with a cathode electrode 81C sandwiched between the outer surface of the detection element 76D and the inner surface of the detection element 76E. An anode electrode 82C is provided on the outer surface of the detection element 76E.

A grounding wire 45 is connected to the cathode electrodes 77A, 77B, 77C, 79A, 79B, 79C, 81A, 81B and 81C. A wire 74 is connected to the anode electrodes 78A, 78B and 78C. A wire 75 is connected to the anode electrodes 80A, 80B and 80C. A wire 76 is connected to the anode electrodes 82A, 82B and 82C. The grounding wire 45 is connected to a connector terminal 7D of the connector section 7. The wire 74 is connected to a connector terminal 7A of the connector section 7. The wire 75 is connected to a connector terminal 7B of the connector section 7. The wire 76 is connected to a connector terminal 7C of the connector section 7. The radiation detectors 5D included in other two columns are likewise connected to other connector terminals provided for the connector section 7. All of the grounding wires 45, 74, 75 and 76 are set in the support substrate 6. Many detector units 4A are attached to a detector support section 23 and held by fitting connector terminals such as the connector terminal 7A provided respectively into the connector section 11 provided for the detector support section 23. As in the case of the detector units 4, many detector units 4A are arranged surrounding the through hole section 41 in the circumferential direction and axial direction of the through hole section 41.

The radiation detectors $5A_1$, $5B_1$ and $5C_1$ comprise three or more detection elements having at least two surfaces, that is, semiconductor elements and arrange anode electrodes and cathode electrodes alternately between different semiconductor elements. More specific explains will be given using the radiation detectors $5A_1$. The radiation detector $5A_1$ comprises anode electrodes and cathode electrodes alternately between different detection elements, that is, between the detection element 74A and detection element 74B, between the detection element 74B and detection element 74C, between the detection element 74C and detection element 74D and between the detection element 74D and detection element 74E, for example, the anode electrode 78A between the detection element 74A and detection element 74B, or the cathode electrode 77B between the detection element 74B and detection element 74C.

When the connector section 7 is engaged with the connector section 11, the three radiation detectors $5A_1$ on the first layer are connected to three signal discriminators 27 in a signal discrimination unit 25 separately. Furthermore, the three radiation detectors $5B_1$ on the second layer and the three radiation detectors $5C_1$ on the third layer are connected to six γ-ray discriminators 32 other than the signal discriminators 27 provided in the signal discrimination unit 25 separately.

The radiological imaging apparatus of this embodiment incorporating the radiation detector units 4A can achieve the effects (1) to (21) produced by the radiological imaging apparatus 1 of Embodiment 1. Furthermore, this embodiment can achieve effects (22) and (23) shown below.

(22) According to this embodiment, the radiation detector 5D has a multilayered structure of a plurality of detection elements, which reduces the thickness of the respective detection elements between the anode electrode and cathode electrode and suppresses reductions of detection signals due to re-coupling between electrons and holes. This improves energy resolution. Furthermore, the time until a detection signal is outputted is shortened and so the time resolution also improves. With the improved energy resolution, it is possible to set a high energy threshold and thereby remove more γ-rays whose energy has decreased due to scattering. Moreover, with the improved time resolution, it is possible to reduce the time window and thereby reduce γ-rays which are detected accidentally within the time window. That is, it is possible to suppress scattering phenomena and accidental phenomena which constitute noise components to a low level and thereby improve the image quality of a PET image.

(23) According to this embodiment, the radiation detector 5D has a multilayered structure of a plurality of detection elements, and therefore the thickness of detection elements between the anode electrode and cathode electrode is reduced and a bias voltage to be applied can be reduced. With a reduced bias voltage, it is possible to reduce a withstand voltage of parts around various wires. Furthermore, the size of the power supply itself can be reduced.

(Embodiment 3)

Figure 13:
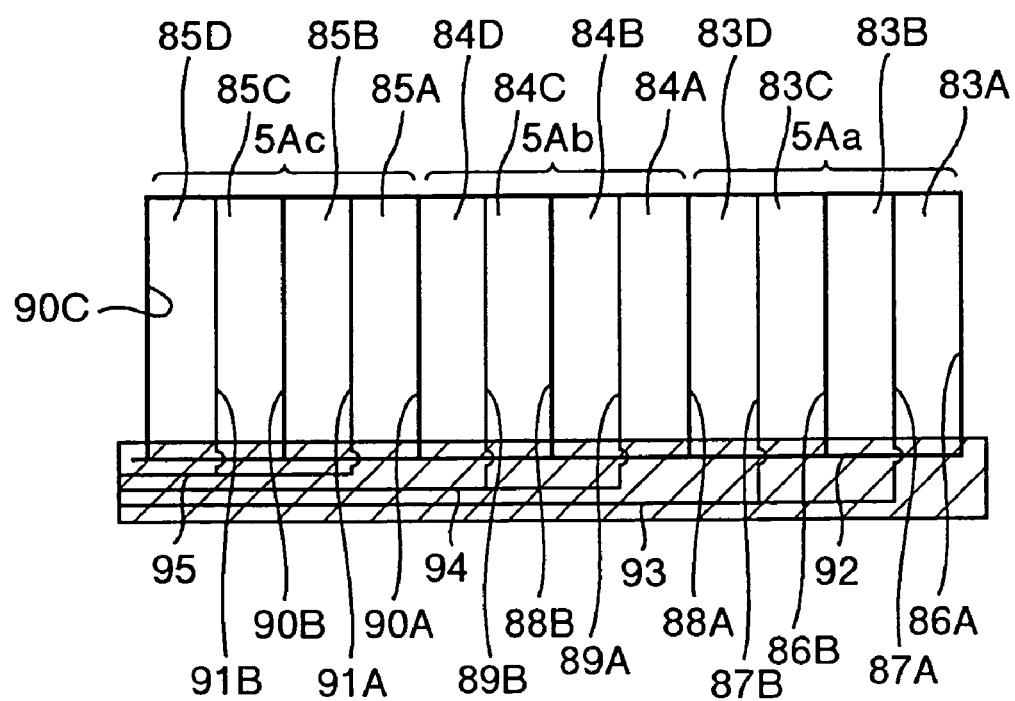
FIG. 13 is a sectional view of the detector support member in the radius direction of the detector unit in FIG. 11.

A radiological imaging apparatus according to Embodiment 3 which is another preferred embodiment of the present invention will be explained below. The radiological imaging apparatus in this embodiment only differs from the configuration of the radiological imaging apparatus 1 of Embodiment 1 in the configuration of the detector unit. A detector unit 4B used in this embodiment having a configuration different from that of the detector unit 4 used in Embodiment 1 will be explained with reference to FIG. 12 and FIG. 13.

The detector unit 4B consists of a plurality (e.g., 9) of radiation detectors 5E arranged in 3 rows and 3 columns on one side of a support substrate 6. Each radiation detector 5E is the same semiconductor radiation detector as the radiation detector 5 and three layers of the radiation detectors 5E are arranged in the radius direction of a detector support member 8. In the radius direction of the detector support member 8, radiation detectors 5Aa, 5Ab and 5Ac, radiation detectors 5Ba, 5Bb and 5Bc, and radiation detectors 5Ca, 5Cb and 5Cc are arranged on the first layer, second layer and third layer respectively. The radiation detectors 5Aa, 5Ab and 5Ac arranged in the circumferential direction of the detector support member 8 are multilayered in the circumferential direction thereof. The radiation detectors 5Ba, 5Bb and 5Bc on the second layer and radiation detectors 5Ca, 5Cb and 5Cc on the third layer are likewise multilayered in the circumferential direction of the detector support member 8. This multilayered structure will be explained by taking the radiation detectors 5Aa, 5Ab and 5Ac as an example.

The radiation detector 5Aa comprises four detection elements, that is, detection elements 83A, 83B, 83C and 83D. The detection elements 83A, 83B, 83C and 83D are arranged in that order in the circumferential direction of the detector support member 8. The radiation detector 5Ab comprises detection elements 84A, 84B, 84C and 84D. The detection elements 84A, 84B, 84C and 84D are arranged in that order in the circumferential direction of the detector support member 8. The radiation detector 5Ac comprises detection elements 85A, 85B, 85C and 85D. The detection elements 85A, 85B, 85C and 85D are arranged in that order in the circumferential direction of the detector support member 8.

A cathode electrode 86A is provided on one side of the detection element 83A. The detection element 83A and detection element 83B are adjacent to each other with an anode electrode 87A sandwiched between the other side of the detection element 83A and one side of the detection element 83B. Here, one side refers to one side of the detection element in the circumferential direction of the detector support member 8 and the other side refers to the remaining side of the detection element in the circumferential direction of the detector support member 8. The detection element 83B and detection element 83C are adjacent to each other with a cathode 86B provided between the other side of the detection element 83B and one side of the detection element 83C. The detection element 83C and detection element 83D are adjacent to each other with an anode 87B provided between the other side of the detection element 83C and one side of the detection element 83D.

The detection element 83D and detection element 84A are adjacent to each other with a cathode electrode 88A provided between the other side of the detection element 83D and one side of the detection element 84A. The detection element 84A and detection element 84B are adjacent to each other with an anode electrode 89A provided between the other side of the detection element 84A and one side of the detection element 84B. The detection element 84B and detection element 84C are adjacent to each other with a cathode electrode 88B provided between the other side of the detection element 84B and one side of the detection element 84C. The detection element 84C and detection element 84D are adjacent to each other with an anode electrode 89B provided between the other side of the detection element 84C and one side of the detection element 84D.

The detection element 84D and detection element 85A are adjacent to each other with a cathode electrode 90A provided between the other side of the detection element 84D and one side of the detection element 85A. The detection element 85A and detection element 85B are adjacent to each other with an anode electrode 91A provided between the other side of the detection element 85A and one side of the detection element 85B. The detection element 85B and detection element 85C are adjacent to each other with a cathode electrode 90B provided between the other side of the detection element 85B and one side of the detection element 85C. The detection element 85C and detection element 85D are adjacent to each other with an anode electrode 91B provided between the other side of the detection element 85C and one side of the detection element 85D. A cathode electrode 90C is provided on the other side of the detection element 85D.

A grounding wire 92 is connected to the cathode electrodes 86A, 86B, 88A, 88B, 90A, 90B and 90C. A wire 93 is connected to the anode electrodes 87A and 87B. A wire 94 is connected to the anode electrodes 89A and 89B. A wire 95 is connected to the anode electrodes 91A and 91B. The grounding wire 92 is connected to a connector terminal 7D of a connector section 7. The wire 93 is connected to a connector terminal 7A of the connector section 7. The wire 94 is connected to a connector terminal 7B of the connector section 7. The wire 95 is connected to a connector terminal 7C of the connector section 7. The radiation detectors 5E on the second layer and third layer are likewise connected to other connector terminals provided on the connector section 7. All of the grounding wire 92 and wires 93, 94 and 95 are set inside the support substrate 6. Many detector units 4B are attached to the detector support section 23 and held by fitting connector terminals such as the connector terminal 7A provided respectively into the connector section 11 provided for the detector support section 23. As in the case of the detector units 4, the detector units 4B are arranged surrounding the through hole section 41 in the circumferential direction and axial direction of the through hole section 41.

When the connector section 7 is engaged with the connector section 11, the radiation detectors 5Aa, 5Ab and 5Ac on the first layer are connected to three signal discriminators 27 in the signal discrimination unit 25 separately. The radiation detectors 5Ba, 5Bb and 5Bc on the second layer and the radiation detectors 5Ca, 5Cb and 5Cc on the third layer are connected to six γ-ray discriminators 32 other than the signal discriminator 27 provided in the signal discrimination unit 25 separately.

The radiological imaging apparatus incorporating the detector units 4B of this embodiment can achieve the effects (1) to (21) produced by the radiological imaging apparatus 1 of Embodiment 1 and the effects (22) and (23) produced by the radiological imaging apparatus of Embodiment 2. Furthermore, this embodiment can achieve the following effect (24).

(24) According to this embodiment, each radiation detector 5E has a multilayered structure of a plurality of detection elements, and therefore it is possible to use both sides of the adjacent radiation detectors 5E as cathode electrodes and allow those radiation detectors 5E to share the cathode electrodes. This allows the three radiation detectors 5E arranged in the circumferential direction of the detector support member 8 to be arranged close to one another. That is, it is possible to completely eliminate spaces between the radiation detectors 5E in the circumferential direction and considerably reduce omissions in γ-ray detection between the radiation detectors 5E in the circumferential direction. This leads to a substantial increase in γ-ray detection efficiency and shortening of an inspection time as well.

Embodiments 1 to 3 have a configuration in which detector units comprising radiation detectors arranged in multilayers in the radius direction of the detector support member 8 (through hole section 41 into which the bed 20 is inserted) are applied to a radiological imaging apparatus which can irradiate X-rays from the X-ray source 17 onto an examinee and detect γ-rays and X-rays. However, the detector units can also be applied to a PET radiological imaging apparatus which does not irradiate X-rays but only detects γ-rays emitted from an examinee caused by radiopharmaceutical which has passed through the examinee. Furthermore, the detector units can also be applied to a SPECT radiological imaging apparatus.

The present invention can improve the accuracy of images created and facilitate replacement of damaged radiation detectors.

It should be further understood by those skilled in the art that although the foregoing description has been made on embodiments of the invention, the invention is not limited thereto and various changes and modifications may be made without departing from the spirit of the invention and the scope of the appended claims.

What is claimed is:

1. A radiological imaging apparatus comprising:
   a detector support section which extends in the longitudinal direction of a bed for supporting an examinee and is arranged around said bed;
   a radiation detection apparatus including a plurality of radiation detector units arranged in the longitudinal direction of said bed and around said bed, said plurality of detector units being attached to said detector support section in a detachable manner, wherein said detector unit comprises a plurality of radiation detectors for detecting radiation and a plurality of said radiation detectors are arranged in a radius direction of said detector support section, wherein said radiation detectors comprise a plurality of semiconductor members, detection signal output electrodes and common potential electrodes, said semiconductor members being arranged in parallel and positioned between said detection signal output electrodes and common potential electrodes; and
   a γ-ray detection signal processing apparatus for obtaining positional information of said radiation detectors outputting γ-ray detection signals, said radiation detectors outputting γ-ray detection signals being arranged in said radius direction.

2. The radiological imaging apparatus according to claim 1, wherein said detector unit comprises:
   a detector support substrate attached to said detector support section in a detachable manner, wherein at least some of said radiation detectors are arranged on said detector support substrate; and
   a plurality of wires provided for said detector support substrate and connected to each of said radiation detectors for transmitting detection signals outputted from said radiation detectors.

3. The radiological imaging apparatus according to claim 2, further comprising an image creation apparatus which creates images of said examinee using the output signals of said radiation detectors.

4. The radiological imaging apparatus according to claim 2, wherein said wires are provided in said detector support substrate.

5. The radiological imaging apparatus according to claim 1, wherein at least one of said radiation detectors comprises a multilayered structure with an even number of semiconductor elements.

6. A radiological imaging apparatus comprising:
   a ring-shaped detector support section which extends in the longitudinal direction of a bed for supporting an examinee and is arranged around said bed;
   a radiation detection apparatus including a plurality of radiation detector units arranged in the longitudinal direction of said bed and in the circumferential direction of said detector support section which includes said plurality of detector units attached to said detector support section in a detachable manner, wherein said detector unit comprises a plurality of radiation detectors for detecting radiation and is provided with a plurality of said radiation detectors in different positions in the radius direction of said detector support section, wherein said radiation detectors comprise a plurality of semiconductor members, detection signal output electrodes and common potential electrodes, said semiconductor members being arranged in parallel and positioned between said detection signal output electrodes and common potential electrodes; and
   a γ-ray detection signal processing apparatus for obtaining positional information of said radiation detectors outputting γ-ray detection signals, said radiation detectors being arranged in said radius direction.

7. The radiological imaging apparatus according to claim 6, wherein said detector unit comprises:
   a detector support substrate attached to said detector support section in a detachable manner;
   at least some of said radiation detectors being arranged on said detector support substrate; and
   a plurality of wires provided for said detector support substrate and connected to each of said radiation detectors for transmitting detection signals outputted from said radiation detectors.

8. The radiological imaging apparatus according to claim 5, further comprising an image creation apparatus which creates images of said examinee using the output signals of said radiation detectors.

9. The radiological imaging apparatus according to claim 6, wherein at least one of said radiation detectors comprises a multilayered structure with an even number of semiconductor elements.

10. A radiological imaging apparatus comprising:
    a detector support section which extends in the longitudinal direction of a bed for supporting an examinee and is arranged around said bed;
    a radiation detection apparatus including a plurality of radiation detector units arranged in the longitudinal direction of said bed and around said bed, said plurality of detector units being attached to said detector support section in a detachable manner, wherein each said detector unit is provided with a plurality of radiation detectors which detect γ-rays and is arranged in a radius direction of said detector support section, wherein said radiation detectors comprise a plurality of semiconductor members, detection signal output electrodes and common potential electrodes, said semiconductor members being arranged in parallel and positioned between said detection signal output electrodes and common potential electrodes; and a signal processing apparatus for processing γ-ray detection signals outputted from said radiation detectors and for obtaining positional information of said radiation detectors outputting γ-ray detection signals on the basis of said γ-ray detection signals, said radiation detectors being arranged in said radius direction.

11. The radiological imaging apparatus according to claim 10, further comprising an image creation apparatus which creates images including areas where radiopharmaceutical in the body of said examinee is concentrated using the output information from said signal processing apparatus.

12. The radiological imaging apparatus according to claim 9, wherein said detector unit comprises:
a detector support substrate attached to said detector support section in a detachable manner;
at least some of said radiation detectors being set in said detector support substrate; and
a plurality of wires provided on said detector support substrate and connected to each of said radiation detectors for transmitting γ-ray detection signals outputted from said radiation detectors, and said signal processing apparatus gets said γ-ray detection signals transmitted through said wires.

13. The radiological imaging apparatus according to claim 12, wherein said wires are provided in said detector support substrate.

14. The radiological imaging apparatus according to claim 12, further comprising an image creation apparatus which creates images including areas where radiopharmaceutical in the body of said examinee is concentrated using the output information from said signal processing apparatus.

15. The radiological imaging apparatus according to claim 14, wherein said wires are provided in said detector support substrate.

16. The radiological imaging apparatus according to claim 10, wherein at least one of said radiation detectors comprises a multilayered structure with an even number of semiconductor elements.

17. A radiological imaging apparatus comprising:
a detector support section which extends in the longitudinal direction of a bed for supporting an examinee and is arranged around said bed;
an X-ray source which moves around said bed and radiates X-rays;
a radiation detection apparatus including a plurality of radiation detector units arranged in the longitudinal direction of said bed and around said bed, said plurality of detector units being attached to said detector support section in a detachable manner, wherein said detector units are provided with a plurality of radiation detectors for detecting radiation, and said radiation detectors are arranged in a radius direction of said radiation detector support member, and at least one of said radiation detectors outputs X-ray detection signals and γ-ray detection signals, wherein said radiation detectors comprise a plurality of semiconductor members, detection signal output electrodes and common potential electrodes, said semiconductor members being arranged in parallel and positioned between said detection signal output electrodes and common potential electrodes; and a γ-ray detection signal processing apparatus for obtaining positional information of said radiation detectors outputting γ-ray detection signals, said radiation detectors being arranged in said radius direction.

18. The radiological imaging apparatus according to claim 16, wherein at least some of said radiation detectors are arranged rectilinearly.

19. The radiological imaging apparatus according to claim 16, further comprising:
a detector support member which extends in the longitudinal direction of a bed for supporting an examinee and is arranged around said bed;
an X-ray source which moves around said bed and radiates X-rays;
a radiation detection apparatus including a plurality of radiation detector units arranged in the longitudinal direction of said bed and around said bed, said plurality of detector units being attached to said detector support member in a detachable manner, wherein each said detector unit is provided with a plurality of radiation detectors for detecting radiation and some of said radiation detectors being for detecting said radiation that has passed through other said radiation detectors, and at least said some radiation detectors output both said X-ray detection signals and γ-ray detection signals; and
an X-ray source transport apparatus which transports said X-ray source in said longitudinal direction.

20. The radiological imaging apparatus according to claim 19, wherein at least some of said radiation detectors are arranged rectilinearly.

21. The radiological imaging apparatus according to claim 16, further comprising a tomographic image creation apparatus which creates tomographic images using first information obtained from said γ-ray detection signals and second information obtained from said X-ray detection signals.

22. The radiological imaging apparatus according to claim 16, further comprising:
a first γ-ray signal processing apparatus for getting said γ-ray detection signals from said first radiation detectors which output both said X-ray detection signals and said γ-ray detection signals and an X-ray signal processing for getting said X-ray detection signals provided for each of said first radiation detectors;
a second γ-ray signal processing apparatus for getting said γ-ray detection signals from said second radiation detectors which do not output said X-ray detection signals but output said γ-ray detection signals provided for each of said second radiation detectors;
a counting apparatus which receives output signals from said first γ-ray signal processing apparatus and said second γ-ray signal processing apparatus and outputs information such as position information of each of a pair of said radiation detectors which have detected said γ-rays within a set time and count information of said detected γ-rays; and
a tomographic image creation apparatus which creates tomographic image information using said position information, said count information and output information of said X-ray signal processing apparatus.

23. The radiological imaging apparatus according to claim 22, wherein said radiation detectors are semiconductor radiation detectors.

24. A radiological imaging apparatus comprising:
a detector support section which extends in the longitudinal direction of a bed for supporting an examinee and is arranged around said bed;
an X-ray source which moves around said bed and radiates X-rays;
a radiation detection apparatus including a plurality of radiation detector units arranged in the longitudinal direction of said bed and around said bed, said plurality of detector units being attached to said detector support section in a detachable manner, wherein each said detector unit is provided with a plurality of semiconductor radiation detectors for detecting radiation and some of said semiconductor radiation detectors being for detecting said radiation that has passed through other said radiation detectors, and at least said some semiconductor radiation detectors output both said X-ray detection signals and γ-ray detection signals;
a first γ-ray signal processing apparatus for getting said γ-ray detection signals from said first semiconductor radiation detectors which output both said X-ray detection signals and said γ-ray detection signals and an X-ray signal processing for getting said X-ray detection signals provided for each of said first semiconductor radiation detectors;
a second γ-ray signal processing apparatus for getting said γ-ray detection signals from said second semiconductor radiation detectors which do not output said X-ray detection signals but output said γ-ray detection signals provided for each of said second semiconductor radiation detectors;
a counting apparatus which receives output signals from said first γ-ray signal processing apparatus and said second γ-ray signal processing apparatus and outputs information such as position information of each of a pair of said semiconductor radiation detectors which have detected said γ-rays within a set time and count information of said detected γ-rays; and
a tomographic image creation apparatus which creates tomographic image information using said position information, said count information and output information of said X-ray signal processing apparatus,
wherein said semiconductor radiation detectors comprise three or more semiconductor elements having at least two surfaces and arrange anode electrodes and cathode electrodes alternately between said different semiconductor elements.

25. A radiological imaging apparatus comprising:
a detector support section which extends in the longitudinal direction of a bed for supporting an examinee and is arranged around said bed;
an X-ray source which moves around said bed and radiates X-rays;
a radiation detection apparatus including a plurality of radiation detector units arranged in the longitudinal direction of said bed and around said bed, said plurality of detector units being attached to said detector support section in a detachable manner, wherein each said detector unit is provided with a plurality of semiconductor radiation detectors for detecting radiation and some of said semiconductor radiation detectors being for detecting said radiation that has passed through other said radiation detectors, and at least said some semiconductor radiation detectors output both said X-ray detection signals and γ-ray detection signals;
a first γ-ray signal processing apparatus for getting said γ-ray detection signals from said first semiconductor radiation detectors which output both said X-ray detection signals and said γ-ray detection signals and an X-ray signal processing for getting said X-ray detection signals provided for each of said first semiconductor radiation detectors;
a second γ-ray signal processing apparatus for getting said γ-ray detection signals from said second semiconductor radiation detectors which do not output said X-ray detection signals but output said γ-ray detection signals provided for each of said second semiconductor radiation detectors;
a counting apparatus which receives output signals from said first γ-ray signal processing apparatus and said second γ-ray signal processing apparatus and outputs information such as position information of each of a pair of said semiconductor radiation detectors which have detected said γ-rays within a set time and count information of said detected γ-rays; and
a tomographic image creation apparatus which creates tomographic image information using said position information, said count information and output information of said X-ray signal processing apparatus,
wherein said semiconductor radiation detector has a multilayered structure with an even number of semiconductor elements, forms common anode electrodes and cathode electrodes between said adjacent semiconductor elements in said semiconductor radiation detectors and forms common cathode electrodes on both the mutually facing sides of the adjacent semiconductor radiation detectors.

26. A radiological imaging apparatus, comprising:
a detector support section which extends in the longitudinal direction of a bed for supporting an examinee and is arranged around said bed;
a radiation detection apparatus including a plurality of radiation detector units arranged in the longitudinal direction of said bed and around said bed, said plurality of detector units being attached to said detector support section in a detachable manner, wherein said detector unit comprises a plurality of radiation detectors for detecting radiation and a plurality of said radiation detectors are arranged in a radius direction of said detector support section, wherein said radiation detectors comprise at least three semiconductor elements each having at least two surfaces, and detection signal output electrodes and common potential electrodes are alternately arranged between said different semiconductor elements;
a γ-ray detection signal processing apparatus for obtaining positional information of said radiation detectors outputting γ-ray detection signals, said radiation detectors outputting γ-ray detection signals being arranged in said radius direction; and
an image creation apparatus which creates images of said examinee using the output signals of said radiation detectors.

27. A radiological imaging apparatus, comprising:
a detector support member which extends in the longitudinal direction of a bed for supporting an examinee and is arranged around said bed;
a radiation detection apparatus including a plurality of radiation detector units arranged in the longitudinal direction of said bed and around said bed, said plurality of detector units being attached to said detector support section in a detachable manner, wherein said detector unit comprises a plurality of radiation detectors for detecting radiation and a plurality of said radiation detectors are arranged in a radius direction of said detector support section, wherein said radiation detectors comprise a plurality of semiconductor members arranged in parallel and detection signal output electrodes and common potential electrodes which are alternatively arranged in connection with said detection signal output electrodes and common potential electrodes;

a γ-ray detection signal processing apparatus for obtaining positional information of said radiation detectors outputting γ-ray detection signals, said radiation detectors outputting γ-ray detection signals being arranged in said radius direction; and an image creation apparatus which creates images of said examinee using the output signals of said radiation detectors.

28. A radiological imaging apparatus, comprising:

a detector support section which extends in the longitudinal direction of a bed for supporting an examinee and is arranged around said bed;

an X-ray source which moves around said bed and radiates X-rays;

a radiation detection apparatus including a plurality of radiation detector units arranged in the longitudinal direction of said bed and around said bed, said plurality of detector units being attached to said detector support section in a detachable manner, wherein said detector units are provided with a plurality of radiation detectors for detecting radiation, and said radiation detectors are arranged in a radius direction of said radiation detector support member, and at least one of said radiation detectors outputs X-ray detection signals and γ-ray detection signals, wherein said radiation detectors comprise a plurality of semiconductor members arranged in parallel and detection signal output electrodes and common potential electrodes which are alternatively arranged in connection with said semiconductor members positioned between said detection signal output electrodes and common potential electrodes; and a γ-ray detection signal processing apparatus for obtaining positional information of said radiation detectors outputting γ-ray detection signals, said radiation detectors being arranged in said radius direction.

* * * * *